| 
US009702869B2

(12) United States Patent
Hu et al.

(10) Patent No.: US 9,702,869 B2
(45) Date of Patent: Jul. 11, 2017

(54) ASSAYS, ANTIBODIES, IMMUNOGENS AND COMPOSITIONS RELATED TO 5-FU

(71) Applicant: WELLSTAT DIAGNOSTICS, LLC, Gaithersburg, MD (US)

(72) Inventors: Paul Q Hu, Frederick, MD (US); Xiaofen Huang, Gaithersburg, MD (US); Reid W Von Borstel, Potomac, MD (US)

(73) Assignee: DEFINED DIAGNOSTICS, LLC, Chevy Chase, MD (US)

( * ) Notice: Subject to any disclaimer, the term of this patent is extended or adjusted under 35 U.S.C. 154(b) by 22 days.

(21) Appl. No.: 14/361,731

(22) PCT Filed: Nov. 30, 2012

(86) PCT No.: PCT/US2012/067353
§ 371 (c)(1),
(2) Date: May 30, 2014

(87) PCT Pub. No.: WO2013/082463
PCT Pub. Date: Jun. 6, 2013

(65) Prior Publication Data
US 2015/0079612 A1    Mar. 19, 2015

Related U.S. Application Data

(60) Provisional application No. 61/665,686, filed on Jun. 28, 2012, provisional application No. 61/565,281, filed on Nov. 30, 2011.

(51) Int. Cl.
*G01N 33/53* (2006.01)
*C07K 16/44* (2006.01)
*G01N 33/94* (2006.01)

(52) U.S. Cl.
CPC ......... *G01N 33/5308* (2013.01); *C07K 16/44* (2013.01); *G01N 33/53* (2013.01); *G01N 33/94* (2013.01); *C07K 2317/33* (2013.01); *G01N 2430/00* (2013.01); *G01N 2800/52* (2013.01)

(58) Field of Classification Search
CPC .... G01N 33/5308; G01N 33/53; G01N 33/94; G01N 2430/00; G01N 2800/52; C07K 16/44; C07K 2317/33
See application file for complete search history.

(56) References Cited

U.S. PATENT DOCUMENTS

| 5,366,862 A * | 11/1994 | Venton ................. B01D 61/145 |
| | | 435/23 |
| 7,205,116 B2 | 4/2007 | Salamone et al. |
| 7,767,794 B2 | 8/2010 | Salamone et al. |
| 2003/0031664 A1 | 2/2003 | Reed |
| 2003/0201208 A1 * | 10/2003 | Koch ................. A61K 49/1863 |
| | | 209/39 |
| 2006/0177883 A1 | 8/2006 | Salamone et al. |
| 2006/0177884 A1 * | 8/2006 | Salamone ............. G01N 33/94 |
| | | 435/7.92 |
| 2008/0138343 A1 | 6/2008 | Law et al. |
| 2009/0130114 A1 | 5/2009 | Qian et al. |
| 2010/0204456 A1 | 8/2010 | Salamone et al. |
| 2010/0239575 A1 | 9/2010 | Banchereau et al. |
| 2010/0297114 A1 * | 11/2010 | Zurawski ............. C07K 14/005 |
| | | 424/133.1 |
| 2011/0014303 A1 * | 1/2011 | McKenna ............ A61K 31/436 |
| | | 424/649 |
| 2011/0034488 A1 | 2/2011 | Roa et al. |
| 2011/0145937 A1 * | 6/2011 | MacDonald ....... A01K 67/0275 |
| | | 800/6 |

OTHER PUBLICATIONS

Australian Patent Examination Report for Application No. 2012327223, Australian Patent Office, dated Apr. 12, 2015.
Partial European Search Report for Application No. EP 12852770.2, European Patent Office, dated Jul. 6 2015.
Salamone, et al., "Novel monoclonal antibodies for measuring 5-fluoruracil concentrations in biological fluids," J Clinical Oncology American Society of Clinical Oncology, Jun. 20, 2006, p. 2055.
Salamone, et al., "Monoclonal antibody 6.8A6.1".14 Performance Characteristics, J Clinical Oncology American Society of Clinical Oncology, Jun. 20, 2006, p. 2055, table 1.
Bertino, et al., "Highlights from: 5-fluorouracil drug management pharmacokinetics and pharmacogenomics workshop; Orlando, Florida; Jan. 2007," Clinical Colorectal Cancer, Mar. 1, 2007, pp. 407-422.
Beumer, et al., "Multicenter Evaluation of a Novel Nanoparticle Immunoassay for 5-Fluorouracil on the Olympus AU400 Analyzer," Ther Drug Monit, vol. 31(6):688-694 (2009).
Honda, et al., "Development and Characterization of a Monoclonal Antibody with Cross-reactivity Towards Uracil and Thymine, and its Potential Use in Screening Patients Treated with 5-Fluorouracil for Possible Risks," Clinica Chimica Acta, vol. 322: 59-66 (2002).
Myriad Genetic Laboratories, Inc., "OnDose® Technical Specifications," Retrieved from https://www.myriad.com/lib/technical-specifications/OnDose%20Tech%20Specs_6_10.pdf (2011).
Saif, et al., "Pharmacokinetically Guided Dose Adjustment of 5-Fluorouracil: A Rational Approach to Improving Therapeutic Outcomes," J Natl Cancer Inst, vol. 101:1543-1552 (2009).
White, et al., "Point-of-Care (POC) Diagnostic Assay for 5-Fluorouracil (5-FU) Quantitation to Enable Dose Adjustment and Detect Dihydropyrimidine Dehydrogenase (DPD) Deficiency," Journal of Clinical Oncology, May 2011, 29(15 suppl):e19562; abstract.
International Search Report for International Application No. PCT/US2012/067353 dated Jun. 19, 2013, and Written Opinion for International Application No. PCT/US2012/067353 dated Jun. 19, 2013.

* cited by examiner

*Primary Examiner* — Galina Yakovleva
*Assistant Examiner* — Nam Nguyen

(57) ABSTRACT

The present invention relates to conjugates of 5-fluorouracil, 5-fluorouracil immunogens, antibodies that bind 5-FU and/or 5-FU conjugated to another molecule, and assays for detecting, quantitating, and monitoring amounts of 5-fluorouracil in a sample such as in blood plasma.

25 Claims, 1 Drawing Sheet

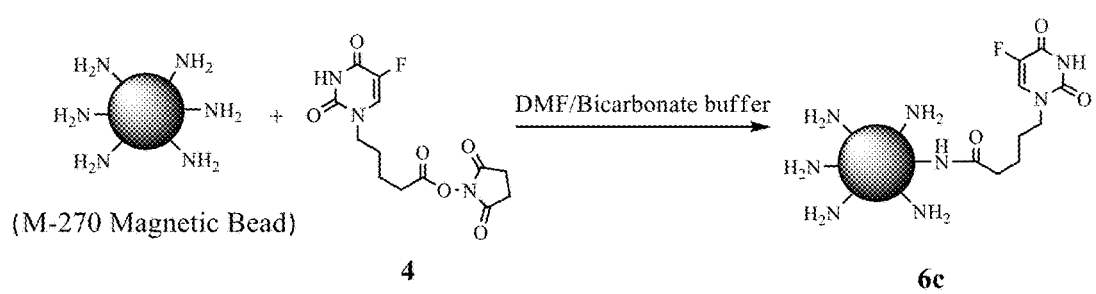
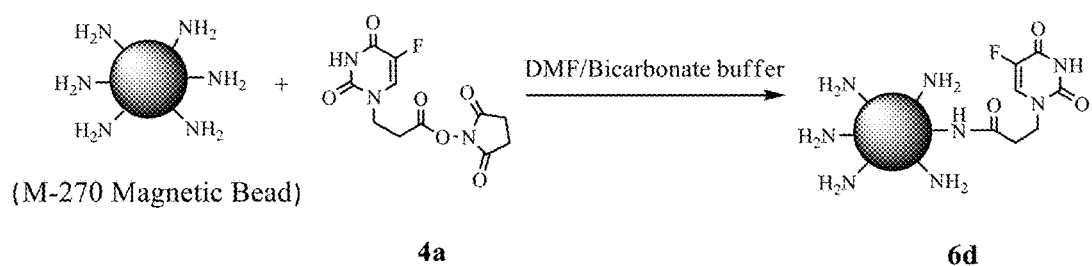

SEQUENCE LISTING

<160> NUMBER OF SEQ ID NOS: 11

<210> SEQ ID NO 1
<211> LENGTH: 4
<212> TYPE: PRT
<213> ORGANISM: Mus musculus

<400> SEQUENCE: 1

Gly Pro Arg Pro
1

<210> SEQ ID NO 2
<211> LENGTH: 477
<212> TYPE: PRT
<213> ORGANISM: Mus musculus

<400> SEQUENCE: 2

Met Asp Trp Leu Trp Asn Leu Leu Phe Leu Met Ala Ala Ala Gln Ser
1               5                   10                  15

Ile Gln Ala Gln Ile Gln Leu Val Gln Ser Gly Pro Glu Leu Lys Lys
            20                  25                  30

Pro Gly Glu Thr Val Thr Ile Ser Cys Lys Ala Ser Gly Tyr Thr Leu
        35                  40                  45

Thr Asn Tyr Gly Met Asn Trp Val Lys Gln Ala Pro Gly Lys Gly Leu
    50                  55                  60

Lys Trp Met Gly Trp Ile Asn Thr Asn Ser Gly Glu Pro Thr Tyr Val
65                  70                  75                  80

Glu Glu Phe Lys Gly Arg Phe Ala Phe Ser Leu Glu Thr Ser Val Ser
                85                  90                  95

Thr Val Tyr Leu Gln Ile Ser Asp Leu Lys His Glu Asp Thr Ala Thr
            100                 105                 110

Tyr Phe Cys Ala Arg Trp Gly Pro His Phe Asn Ala Tyr Gly Trp Phe
        115                 120                 125

Ala Tyr Trp Gly Gln Gly Thr Leu Val Thr Val Ser Ala Ala Lys Thr
    130                 135                 140

Thr Pro Pro Ser Val Tyr Pro Leu Ala Pro Gly Cys Gly Asp Thr Thr
145                 150                 155                 160

Gly Ser Ser Val Thr Leu Gly Cys Leu Val Lys Gly Tyr Phe Pro Glu
                165                 170                 175

Ser Val Thr Val Thr Trp Asn Ser Gly Ser Leu Ser Ser Ser Val His
            180                 185                 190

Thr Phe Pro Ala Leu Leu Gln Ser Gly Leu Tyr Thr Met Ser Ser Ser
        195                 200                 205

Val Thr Val Pro Ser Ser Thr Trp Pro Ser Gln Thr Val Thr Cys Ser
    210                 215                 220

Val Ala His Pro Ala Ser Ser Thr Thr Val Asp Lys Lys Leu Glu Pro
225                 230                 235                 240

Ser Gly Pro Ile Ser Thr Ile Asn Pro Cys Pro Pro Cys Lys Glu Cys
                245                 250                 255

His Lys Cys Pro Ala Pro Asn Leu Glu Gly Gly Pro Ser Val Phe Ile
            260                 265                 270

Phe Pro Pro Asn Ile Lys Asp Val Leu Met Ile Ser Leu Thr Pro Lys
        275                 280                 285

Val Thr Cys Val Val Val Asp Ser Glu Asp Pro Asp Val Gln
    290                 295                 300

```
Ile Ser Trp Phe Val Asn Asn Val Glu Val His Thr Ala Gln Thr Gln
305                 310                 315                 320

Thr His Arg Glu Asp Tyr Asn Ser Thr Ile Arg Val Val Ser Thr Leu
            325                 330                 335

Pro Ile Gln His Gln Asp Trp Met Ser Gly Lys Glu Phe Lys Cys Lys
            340                 345                 350

Val Asn Asn Lys Asp Leu Pro Ser Pro Ile Glu Arg Thr Ile Ser Lys
        355                 360                 365

Ile Lys Gly Leu Val Arg Ala Pro Gln Val Tyr Ile Leu Pro Pro Pro
    370                 375                 380

Ala Glu Gln Leu Ser Arg Lys Asp Val Ser Leu Thr Cys Leu Val Val
385                 390                 395                 400

Gly Phe Asn Pro Gly Asp Ile Ser Val Glu Trp Thr Ser Asn Gly His
            405                 410                 415

Thr Glu Glu Asn Tyr Lys Asp Thr Ala Pro Val Leu Asp Ser Asp Gly
            420                 425                 430

Ser Tyr Phe Ile Tyr Ser Lys Leu Asn Met Lys Thr Ser Lys Trp Glu
        435                 440                 445

Lys Thr Asp Ser Phe Ser Cys Asn Val Arg His Glu Gly Leu Lys Asn
    450                 455                 460

Tyr Tyr Leu Lys Lys Thr Ile Ser Arg Ser Pro Gly Lys
465                 470                 475

<210> SEQ ID NO 3
<211> LENGTH: 10
<212> TYPE: PRT
<213> ORGANISM: Mus musculus

<400> SEQUENCE: 3

Gly Tyr Thr Leu Thr Asn Tyr Gly Met Asn
1               5                   10

<210> SEQ ID NO 4
<211> LENGTH: 17
<212> TYPE: PRT
<213> ORGANISM: Mus musculus

<400> SEQUENCE: 4

Trp Ile Asn Thr Asn Ser Gly Glu Pro Thr Tyr Val Glu Glu Phe Lys
1               5                   10                  15

Gly

<210> SEQ ID NO 5
<211> LENGTH: 13
<212> TYPE: PRT
<213> ORGANISM: Mus musculus

<400> SEQUENCE: 5

Trp Gly Pro His Phe Asn Ala Tyr Gly Trp Phe Ala Tyr
1               5                   10

<210> SEQ ID NO 6
<211> LENGTH: 234
<212> TYPE: PRT
<213> ORGANISM: Mus musculus
```

```
<400> SEQUENCE: 6

Met Met Ser Ser Ala Gln Phe Leu Gly Leu Leu Leu Leu Cys Phe Gln
1               5                   10                  15

Gly Thr Arg Cys Tyr Ile Gln Met Thr Gln Thr Ala Ser Ser Leu Ser
            20                  25                  30

Ala Ser Leu Gly Asp Arg Val Thr Ile Ser Cys Arg Ala Ser Gln Asp
        35                  40                  45

Ile Trp Asn Tyr Leu Asn Trp Tyr Gln Gln Lys Pro Asp Gly Thr Ile
    50                  55                  60

Lys Leu Leu Ile Tyr Tyr Lys Ser Arg Leu His Ser Gly Val Pro Ser
65                  70                  75                  80

Arg Phe Ser Gly Ser Gly Ser Gly Ile Asp Phe Ser Leu Thr Ile Ser
                85                  90                  95

Asn Leu Glu Gln Glu Asp Phe Ala Thr Tyr Phe Cys Gln Gln Gly His
            100                 105                 110

Thr Leu Pro Trp Thr Phe Gly Gly Gly Ser Lys Leu Glu Ile Lys Arg
        115                 120                 125

Ala Asp Ala Ala Pro Thr Val Ser Ile Phe Pro Pro Ser Ser Glu Gln
    130                 135                 140

Leu Thr Ser Gly Gly Ala Ser Val Val Cys Phe Leu Asn Asn Phe Tyr
145                 150                 155                 160

Pro Lys Asp Ile Asn Val Lys Trp Lys Ile Asp Gly Ser Glu Arg Gln
                165                 170                 175

Asn Gly Val Leu Asn Ser Trp Thr Asp Gln Asp Ser Lys Asp Ser Thr
            180                 185                 190

Tyr Ser Met Ser Ser Thr Leu Thr Leu Thr Lys Asp Glu Tyr Glu Arg
        195                 200                 205

His Asn Ser Tyr Thr Cys Glu Ala Thr His Lys Thr Ser Thr Ser Pro
    210                 215                 220

Ile Val Lys Ser Phe Asn Arg Asn Glu Cys
225                 230

<210> SEQ ID NO 7
<211> LENGTH: 11
<212> TYPE: PRT
<213> ORGANISM: Mus musculus

<400> SEQUENCE: 7

Arg Ala Ser Gln Asp Ile Trp Asn Tyr Leu Asn
1               5                   10

<210> SEQ ID NO 8
<211> LENGTH: 7
<212> TYPE: PRT
<213> ORGANISM: Mus musculus

<400> SEQUENCE: 8

Tyr Lys Ser Arg Leu His Ser
1               5

<210> SEQ ID NO 9
<211> LENGTH: 9
<212> TYPE: PRT
<213> ORGANISM: Mus musculus

<400> SEQUENCE: 9

Gln Gln Gly His Thr Leu Pro Trp Thr
1               5
```

```
<210> SEQ ID NO 10
<211> LENGTH: 1434
<212> TYPE: DNA
<213> ORGANISM: Mus musculus

<400> SEQUENCE: 10
atggattggc tgtggaactt gctattcctg atggcagctg cccaaagtat ccaagcacag      60
atccagttgg tgcagtctgg acctgagctg aagaagcctg agagacagt cacgatctcc     120 tgcaaggctt ctggatatac cctcacaaac tatggaatga actgggtgaa gcaggctcca     180
ggaaagggtt taaagtggat gggctggata acaccaatt ctggagaacc aacatacgtt      240
gaagagttca agggacggtt tgccttctct ttggaaacct ctgtcagcac tgtctatttg     300
caaatcagtg acctcaaaca tgaggacacg ctacatatt tctgtgcaag atggggcccc     360
catttcaacg cctacgggtg gtttgcttat tggggccaag ggactctggt cactgtctct     420
gcagccaaaa caacaccccc atcagtctat ccactggccc tgggtgtgg agatacaact      480 ggttcctccg tgactctggg atgcctggtc aagggctact ccctgagtc agtgactgtg      540 acttggaact ctggatccct gtccagcagt gtgcacacct tcccagctct cctgcagtct     600
ggactctaca ctatgagcag ctcagtgact gtcccctcca gcacctggcc aagtcagacc     660
gtcacctgca gcgttgctca cccagccagc agcaccacgg tggacaaaaa acttgagccc     720
agcgggccca tttcaacaat caaccccgt cctccatgca aggagtgtca caatgccca      780 gctcctaacc tcgagggtgg accatccgtc ttcatcttcc ctccaaatat caaggatgta     840
ctcatgatct ccctgacacc caaggtcacg tgtgtggtgg tggatgtgag cgaggatgac     900
ccagacgtcc agatcagctg gtttgtgaac aacgtggaag tacacacagc tcagacacaa     960
acccatagag aggattacaa cagtactatc cgggtggtca gcaccctccc catccagcac    1020
caggactgga tgagtggcaa ggagttcaaa tgcaaggtca acaacaaaga cctcccatca    1080
cccatcgaga gaaccatctc aaaaattaaa gggctagtca gagctccaca agtatacatc    1140
ttgccgccac cagcagagca gttgtccagg aaagatgtca gtctcacttg cctggtcgtg    1200
ggcttcaacc ctggagacat cagtgtggag tggaccagca atgggcatac agaggagaac    1260
tacaaggaca ccgcaccagt cctggactct gacggttctt acttcatata tagcaagctc    1320
aatatgaaaa caagcaagtg ggagaaaaca gattccttct catgcaacgt gagacacgag    1380
ggtctgaaaa attactacct gaagaagacc atctcccggt ctccgggtaa atga          1434

<210> SEQ ID NO 11
<211> LENGTH: 705
<212> TYPE: DNA
<213> ORGANISM: Mus musculus

<400> SEQUENCE: 11
atgatgtcct ctgctcagtt ccttggtctc ctgttgctct gttttcaagg taccagatgt      60
tatatccaga tgacacagac tgcatcctcc ctgtctgcct ctctgggaga cagagtcacc     120
atcagttgca gggcaagtca ggacattgg aattatttaa actggtatca gcagaaacca     180
gatggaacta ttaaactcct gatctactat aaatcaagat tacactcagg agtcccatca     240
aggttcagtg gcagtgggtc tggaatagat ttttctctca ccattagcaa cctggaacaa     300
gaagattttg ccacttactt ttgccaacag ggtcatacgc ttccgtggac gttcggtgga     360
ggctccaaac tggagatcaa acgggctgat gctgcaccaa ctgtatccat cttcccacca     420
tccagtgagc agttaacatc tggaggtgcc tcagtcgtgt gcttcttgaa caacttctac     480
```

```
cccaaagaca tcaatgtcaa gtggaagatt gatggcagtg aacgacaaaa tggcgtcctg    540
aacagttgga ctgatcagga cagcaaagac agcacctaca gcatgagcag caccctcacg    600
ttgaccaagg acgagtatga acgacataac agctatacct gtgaggccac tcacaagaca    660
tcaacttcac ccattgtcaa gagcttcaac aggaatgagt gttag                    705
```

ASSAYS, ANTIBODIES, IMMUNOGENS AND COMPOSITIONS RELATED TO 5-FU

This is a national stage application of International Application No. PCT/US2012/067353, filed internationally on Nov. 30, 2012, which claims priority to U.S. Provisional Patent Application Nos. 61/565,281 and 61/665,686, filed on Nov. 30, 2011 and Jun. 28, 2012, respectively, each of which is incorporated by reference herein in its entirety.

FIELD

The present disclosure relates to assays for detecting the presence and quantitating or monitoring amounts of 5-Fluorouracil (5-FU) in biological samples.

BACKGROUND

5-Fluorouracil (5-FU) is widely used in cancer patients to treat tumors including, but not limited to, colorectal, head and neck, stomach and breast carcinomas. 5-FU is most often administered systemically, but is also applied topically to treat some forms of pre-cancerous and cancerous skin disorders. Prodrugs of 5-FU are also used in cancer treatment.

5-FU pharmacokinetics have been shown to have a wide interpatient and intrapatient variability. There are still several uncertainties surrounding the rates of metabolism of 5-FU between individuals, including differences between regulated doses among patients. For example, when equal doses of 5-FU, prepared based on calculated body surface area per individual, are administered to different patients, marked differences in systemic exposures occurs. (Bertino et al., Clin. Colorectal Cancer, 6:407-426, (2007)). This can lead to toxicity as a result of overdosing in some patients, or reduced efficacy due to underdosing in others. Additionally, some patients have a dihydropyrimidine dehydrogenase (DPD) deficiency, which can cause very severe, possibly lethal, toxic side-effects from 5-FU exposure. In fact, some patients, particularly geriatric patients, have reduced 5-FU plasma clearance which leads to a higher risk of toxicity.

Accordingly, it is critical to design effective routine therapeutic drug management systems for administering and monitoring the levels of 5-FU in the body so that the toxic or ineffective doses can be adjusted in a timely manner to limit and avoid any undesired side-effects in patients. For example, the ability to individualize dose adjustments of 5-FU to a target plasma level would be more accurate and preferred to a method of dosing based on body surface area. Individualized dosing would also lead to decreased incidents of toxicity, improved survival rates and increased overall response of patients to the 5-FU treatment. There exists a need for improved antibodies, immunoassays and methods for monitoring 5-FU levels so that 5-FU doses can be adjusted to achieve optimal plasma concentrations.

SUMMARY

The present disclosure relates generally to conjugates of 5-fluorouracil, 5-fluorouracil immunogens, antibodies that bind 5-FU and/or 5-FU conjugated to another molecule, and assays for detecting, quantitating, and monitoring amounts of 5-fluorouracil in a sample such as in blood plasma.

The present disclosure relates generally to an antibody that binds to 5-FU and has 2.4% or less cross-reactivity with uracil in a competitive assay.

In some embodiments, the disclosure relates generally to an antibody that binds to 5-FU and has 2.4% or less cross-reactivity with uracil in a competitive assay, wherein the antibody that binds to 5-FU and has less than 3% cross-reactivity with thymine in a competitive assay.

The present disclosure relates generally to an antibody that binds to 5-FU and has less than 3% cross-reactivity with thymine in a competitive assay.

In some embodiments, the disclosure relates generally to antibodies of the present disclosure, wherein the antibody has more than 15% cross-reactivity with tegafur in a competitive assay.

In some embodiments, the disclosure relates generally to antibodies of the present disclosure, wherein the antibody has less than 1% cross reactivity with one or more compounds selected from the group consisting of capecitabine, uracil, uridine, thymine, thymidine, folinic acid, oxaliplatin, irinotecan, methotrexate and cisplatin.

In some embodiments, the disclosure relates generally to antibodies of the present disclosure, wherein the antibody has less than 3% cross reactivity with 5,6-dihydro-5-fluorouracil.

The present disclosure relates generally to an isolated antibody or fragment thereof that binds 5-FU, the antibody comprising a heavy and light chain, wherein the heavy chain amino acid sequence comprises SEQ ID NOs: 3, 4 and 5 and wherein the light chain amino acid sequence comprises SEQ ID NOs: 7, 8 and 9.

In some embodiments, the disclosure relates generally to an isolated antibody or fragment thereof that binds 5-FU, wherein the heavy chain amino acid sequence comprises amino acids 20-477 of SEQ ID NO:2.

In some embodiments, the disclosure relates generally to an isolated antibody or fragment thereof that binds 5-FU, wherein the light chain amino acid sequence comprises amino acids 21-234 of SEQ ID NO:6.

In some embodiments, the disclosure relates generally to an isolated antibody or fragment thereof that binds 5-FU, wherein the antibody is selected from the group consisting of a monoclonal antibody, a humanized antibody; a chimeric antibody; a single-chain Fv (scFv); an Fab fragment; an F(ab') fragment; and a synthetic antibody.

The present disclosure relates generally to compounds of the formula (1):

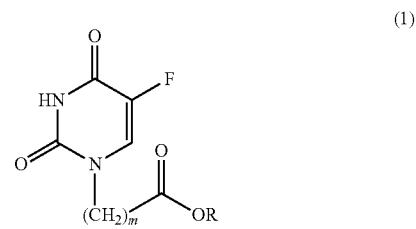

(1)

wherein R is a protein, N-Hydroxysuccinimide (NHS), a detection label or taken together with its attached oxygen atom forms a reactive ester and wherein m=1, 2, 3 or 4.

In some embodiments, the disclosure relates generally to compounds of formula (1), wherein the formula is:

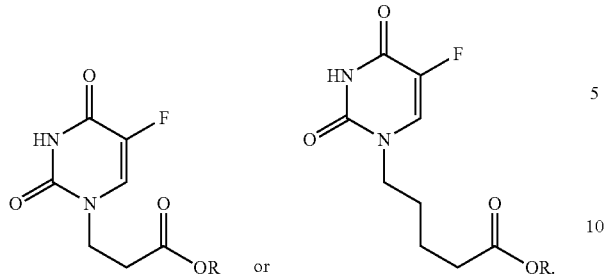

In some embodiments, the disclosure relates generally to compounds of formula (1), wherein R forms a reactive ester.

In some embodiments, the disclosure relates generally to compounds of formula (1), wherein the ester formed is a lower alkyl ester, imidoester or amidoester.

In some embodiments, the disclosure relates generally to compounds of formula (1), wherein the protein is selected from the group consisting of keyhole limpet hemocyanin (KLH) and serum albumin.

In some embodiments, the disclosure relates generally to compounds of formula (1), wherein the label is selected from the group consisting of an electrochemiluminescence label, an enzyme label, a fluorophore, a latex particle, a magnetic particle, a radioactive element, a phosphorescent dye, a dye crystalite, a gold particle, a silver colloidal particle, a selenium colloidal particle, a metal chelate, a coenzyme, an electro active group, an oligonucleotide and a stable radical.

In some embodiments, the disclosure relates generally to compounds of formula (1), wherein the metal chelate is a ruthenium or an osmium metal chelate.

In some embodiments, the disclosure relates generally to compounds of formula (1), wherein the compound is:

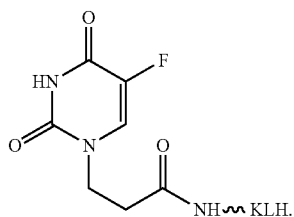

In some embodiments, the disclosure relates generally to compounds of formula (1), wherein the compound is

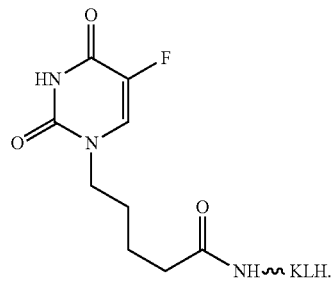

The present disclosure relates generally to methods of producing an antibody that binds selectively to 5-fluorouracil (5-FU) comprising:

a) immunizing an animal with at least one compound of the formula (1):

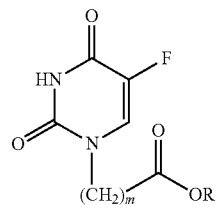

wherein R is a protein, N-Hydroxysuccinimide (NHS), a protein, a detection label or taken together with its attached oxygen atom forms a reactive ester and $m=1$, 2, 3 or 4; and b) isolating the antibody.

In some embodiments, the disclosure relates generally to methods of producing an antibody that binds selectively to 5-fluorouracil (5-FU), wherein the mammal is immunized with the compound of the formula:

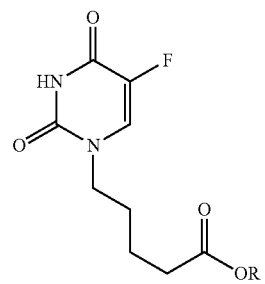

In some embodiments, the disclosure relates generally to methods of producing an antibody that binds selectively to 5-fluorouracil (5-FU), wherein the mammal is immunized with the compound of the formula:

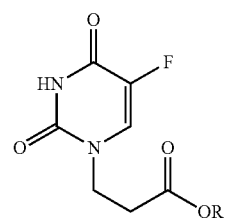

In some embodiments, the disclosure relates generally to methods of producing an antibody that binds selectively to 5-fluorouracil (5-FU), wherein the antibody is a monoclonal antibody.

In some embodiments, the disclosure relates generally to methods of producing an antibody that binds selectively to 5-fluorouracil (5-FU), wherein the antibody binds to 5-FU and has 2.4% or less cross-reactivity with uracil in a competitive assay.

In some embodiments, the disclosure relates generally to methods of producing an antibody that binds selectively to 5-fluorouracil (5-FU), wherein the antibody binds to 5-FU and has less than 3% cross-reactivity with thymine in a competitive assay.

In some embodiments, the disclosure relates generally to methods of producing an antibody that binds selectively to 5-fluorouracil (5-FU), wherein the antibody binds to 5-FU and has more than 15% cross-reactivity with tegafur in a competitive assay.

In some embodiments, the disclosure relates generally to methods of producing an antibody that binds selectively to 5-fluorouracil (5-FU), wherein the antibody has less than 1% cross reactivity with one or more compounds selected from the group consisting of capecitabine, uracil, uridine, thymine, thymidine, folinic acid, oxaliplatin, irinotecan, methotrexate and cisplatin.

In some embodiments, the disclosure relates generally to methods of producing an antibody that binds selectively to 5-fluorouracil (5-FU), wherein the antibody has less than 3% cross reactivity with 5,6-dihydro-5-fluorouracil.

In some embodiments, the disclosure relates generally to methods of producing an antibody that binds selectively to 5-fluorouracil (5-FU), wherein the antibody is a murine IgG2b antibody.

The present disclosure relates generally to an antibody produced by any one of the methods of the present disclosure.

The present disclosure relates generally to methods of detecting 5-fluorouracil (5-FU) in a sample comprising combining in a solution at least said sample with a first binding molecule and a detector molecule, wherein the first binding molecule can bind the detector molecule and wherein 5-FU competitively inhibits the binding of the first binding molecule to the detector molecule and detecting the binding of the first binding molecule to the detector molecule.

In some embodiments, the disclosure relates generally to methods of detecting 5-fluorouracil (5-FU) in a sample, wherein the sample is a serum sample from a mammal.

In some embodiments, the disclosure relates generally to methods of detecting 5-fluorouracil (5-FU) in a sample, wherein the first binding molecule is an antibody or fragment thereof.

In some embodiments, the disclosure relates generally to methods of detecting 5-fluorouracil (5-FU) in a sample, wherein the antibody or fragment thereof binds to 5-FU and has 2.4% or less cross-reactivity with uracil in a competitive assay.

In some embodiments, the disclosure relates generally to methods of detecting 5-fluorouracil (5-FU) in a sample, wherein the antibody binds to 5-FU and has less than 3% cross-reactivity with thymine in a competitive assay.

In some embodiments, the disclosure relates generally to methods of detecting 5-fluorouracil (5-FU) in a sample, wherein the antibody has more than 15% cross-reactivity with tegafur in a competitive assay.

In some embodiments, the disclosure relates generally to methods of detecting 5-fluorouracil (5-FU) in a sample, wherein the antibody has less than 1% cross reactivity with one or more compounds selected from the group consisting of capecitabine, uracil, uridine, thymine, thymidine, folinic acid, oxaliplatin, irinotecan, methotrexate and cisplatin.

In some embodiments, the disclosure relates generally to methods of detecting 5-fluorouracil (5-FU) in a sample, wherein the antibody has less than 3% cross reactivity with 5,6-dihydro-5-fluorouracil.

In some embodiments, the disclosure relates generally to methods of detecting 5-fluorouracil (5-FU) in a sample, wherein the sample is diluted prior to combining with the first binding molecule.

In some embodiments, the disclosure relates generally to methods of detecting 5-fluorouracil (5-FU) in a sample, wherein the sample is not diluted prior to combining with the first binding molecule.

In some embodiments, the disclosure relates generally to methods of detecting 5-fluorouracil (5-FU) in a sample, wherein the sample is blood plasma.

In some embodiments, the disclosure relates generally to methods of detecting 5-fluorouracil (5-FU) in a sample, wherein at least the first binding molecule or the detector molecule is from a lyophilized composition that is rehydrated with the sample.

In some embodiments, the disclosure relates generally to methods of detecting 5-fluorouracil (5-FU) in a sample, wherein the first binding molecule is from a lyophilized composition.

In some embodiments, the disclosure relates generally to methods of detecting 5-fluorouracil (5-FU) in a sample, wherein the detector molecule is from a lyophilized composition.

In some embodiments, the disclosure relates generally to methods of detecting 5-fluorouracil (5-FU) in a sample, wherein the first binding molecule and the detector molecule are lyophilized in separate compositions.

In some embodiments, the disclosure relates generally to methods of detecting 5-fluorouracil (5-FU) in a sample, wherein the separate lyophilized compositions are rehydrated with the sample.

In some embodiments, the disclosure relates generally to methods of detecting 5-fluorouracil (5-FU) in a sample, wherein the method has a lower detection limit of <5.0 ng/mL.

In some embodiments, the disclosure relates generally to methods of detecting 5-fluorouracil (5-FU) in a sample, wherein the method has a dynamic range of 10-30,000 ng/mL.

In some embodiments, the disclosure relates generally to methods of detecting 5-fluorouracil (5-FU) in a sample, wherein the method is completed in less than 3, 5, 7, 10, 12 or 15 minutes.

In some embodiments, the disclosure relates generally to methods of detecting 5-fluorouracil (5-FU) in a sample, wherein the sample is from a patient and the method further comprises adjusting a patient's dose of 5-FU based on the amount of 5-FU detected in the sample.

In some embodiments, the disclosure relates generally to methods of detecting 5-fluorouracil (5-FU) in a sample, wherein the solution comprises GPRP-$NH_2$ (SEQ ID NO:1).

In some embodiments, the disclosure relates generally to methods of detecting 5-fluorouracil (5-FU) in a sample, wherein the first binding molecule is bound to a surface.

In some embodiments, the disclosure relates generally to methods of detecting 5-fluorouracil (5-FU) in a sample, wherein after the solution is incubated for a period of time, the first binding molecule is then bound to a surface.

In some embodiments, the disclosure relates generally to methods of detecting 5-fluorouracil (5-FU) in a sample, wherein the first binding molecule and the surface each are comprised of a corresponding member of a binding pair.

In some embodiments, the disclosure relates generally to methods of detecting 5-fluorouracil (5-FU) in a sample, wherein the binding pair is streptavidin and biotin.

In some embodiments, the disclosure relates generally to methods of detecting 5-fluorouracil (5-FU) in a sample, wherein the first binding molecule comprises biotin.

In some embodiments, the disclosure relates generally to methods of detecting 5-fluorouracil (5-FU) in a sample, wherein the surface is a bead.

In some embodiments, the disclosure relates generally to methods of detecting 5-fluorouracil (5-FU) in a sample, wherein the bead is a paramagnetic bead.

In some embodiments, the disclosure relates generally to methods of detecting 5-fluorouracil (5-FU) in a sample, wherein the at least one detection label is selected from an electrochemiluminescence label, an enzyme label, a fluorophore, a latex particle, a magnetic particle, a radioactive element, a phosphorescent dye, a dye crystalite, a gold particle, a silver colloidal particle, a selenium colloidal particle, a metal chelate, a coenzyme, an electro active group, an oligonucleotide and a stable radical.

In some embodiments, the disclosure relates generally to methods of detecting 5-fluorouracil (5-FU) in a sample, wherein the metal chelate is a ruthenium or an osmium metal chelate.

In some embodiments, the disclosure relates generally to methods of detecting 5-fluorouracil (5-FU) in a sample, wherein the mammal is a human.

The present disclosure relates generally to ECL detection kits for detecting 5-FU in a sample, the kit comprising a binding molecule optionally immobilized or bound to a surface; and a labeled detector molecule, wherein the binding molecule can bind the detector molecule and wherein 5-FU competitively inhibits binding of the binding molecule to the detector molecule. The kit can also comprise the use of a portable ECL analyzer.

The present disclosure generally relates to assays for detecting 5-FU in a sample. In some embodiments, assays of the present disclosure are capable of accurately monitoring 5-FU in a sample (e.g., plasma), providing results over a wide dynamic range. Assays of the present disclosure permit monitoring of 5-FU during infusion and/or after oral administration of 5-FU prodrugs. This can be used for identifying patients overexposed to 5-FU due to DPD deficiency or other clearance problems. Additionally, assays of the present disclosure can be used for individualized 5-FU treatment, which can result in improved efficacy and diminished side effects.

BRIEF DESCRIPTION OF THE SEQUENCES

SEQ ID NO:1 is the amino acid sequence GPRP.
SEQ ID NO:2 is the amino acid sequence of the heavy chain of the monoclonal antibody 61C6 (mab 61C6).
SEQ ID NOs:3, 4 and 5 are the amino acid sequences of the CDR1, CDR2 and CDR3, respectively, of the heavy chain of mab 61C6.
SEQ ID NO:6 is the amino acid sequence of the light chain of mab 61C6.
SEQ ID NOs:7, 8 and 9 are the amino acid sequences of the CDR1, CDR2 and CDR3, respectively, of the light chain of mab 61C6.
SEQ ID NO:10 is a nucleotide sequence coding for the heavy chain of mab 61C6.
SEQ ID NO:11 is a nucleotide sequence coding for the light chain of mab 61C6.

BRIEF DESCRIPTION OF THE DRAWINGS

FIG. 1 is a schematic representation of the chemical formulation to prepare 1-5C-5-FU-M270 beads and 1-3C-5-FU-M270 beads as described in Example 15.

DETAILED DESCRIPTION

The present disclosure provides a variety of antibodies which selectively bind to 5-FU. These antibodies are derived from compounds or immunogens of formula (1) shown below. The antibodies are used in immunoassays that can advantageously detect, quantitate and monitor amounts of 5-FU in a biological sample. The immunoassays for measuring 5-FU in biological samples are rapid, sensitive and accurate thereby optimizing dosing of 5-FU during treatment.

Immunogens

The present disclosure relates generally to compounds of formula (1):

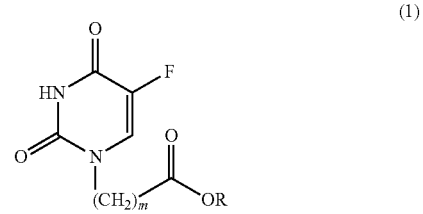

wherein R is a protein, N-Hydroxysuccinimide (NHS), a detection label or taken together with its attached oxygen atom forms a reactive ester and wherein m=1, 2, 3 or 4. The compounds of formula (1) are conjugates of 5-FU that are designed to compete with 5-FU in the sample for binding sites on the antibodies of the present disclosure. The immunogen compounds presently disclosed are 1-substituted 5-FU derivatives of compounds of formula (1).

In certain embodiments of the present disclosure, a compound of formula (1) can be any one of the following:

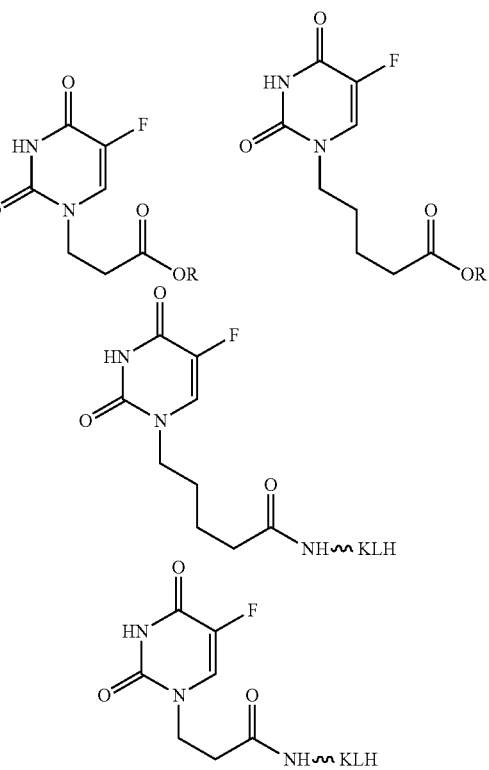

-continued

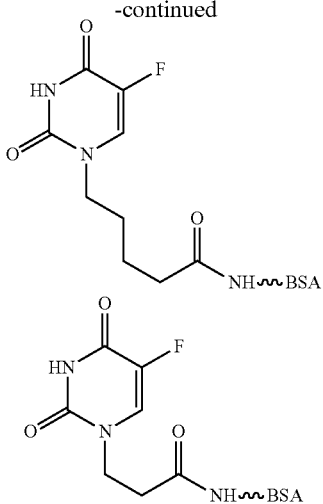

wherein R is a protein, N-Hydroxysuccinimide (NHS), a detection label or taken together with its attached oxygen atom forms a reactive ester. In certain embodiments, the ester formed can be a lower alkyl ester, imidoester or amidoester. In still other embodiments, a protein can be a keyhole limpet hemocyanin (KLH) and/or a serum albumin, such as, for example, bovine serum albumin (BSA). A protein and/or detection label can be linked to the compound by any means including by reacting with NHS. It is contemplated that the detection label can be attached or bound to the protein such as to BSA or KLH. The binding or attachment to the protein can be accomplished with carbon linkers of various lengths and arrangements including, but not limited to, 2-, 3-, 4-, or 5-carbon chains, and straight, branched, saturated or unsaturated carbon chains. Other atoms besides carbon may be included in these linkers as well, including oxygen, nitrogen and sulfur, for example.

In some embodiments, a detection label is selected from the group consisting of an electrochemiluminescence label, an enzyme label, a fluorophore, a latex particle, a magnetic particle, a radioactive element, a phosphorescent dye, a dye crystalite, a gold particle, a silver colloidal particle, a selenium colloidal particle, a metal chelate, a coenzyme, an electro active group, an oligonucleotide and a stable radical. Examples of suitable metal chelates include, but are not limited to, ruthenium or osmium metal chelates.

Production of Anti-5-FU Antibodies

The antibodies of the present disclosure that bind selectively to 5-FU can be produced by immunizing an animal with at least one compound of the formula (1):

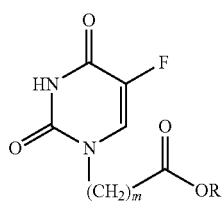

(1)

wherein R is a protein and wherein m=1, 2, 3 or 4, and then isolating the antibody. A protein can be linked to the compound by any means including by reacting with NHS. The antibodies of the present invention are generated from a position-1 modified conjugate of 5-FU with shorter linkers (see, e.g., Examples 4 and 6). In some embodiments, an animal is immunized with at least one compound of the formula:

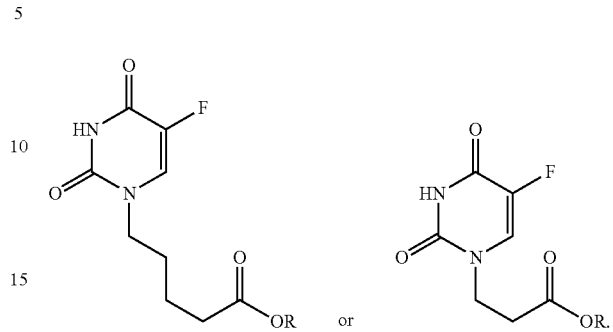

It is contemplated that in certain embodiments, both compounds above can be used to immunize an animal. It is further contemplated that in other embodiments, only one of these two compounds above will be used to immunize an animal.

The methods for producing the antibodies of the present disclosure include those to make polyclonal or monoclonal antibodies. The animals being immunized can be birds or mammals, including those selected from the group consisting of a mouse, a rat, a rabbit, a bovine, a horse, a dog, a cat, a goat, a sheep, and a pig.

In certain embodiments, the methods for producing antibodies of the present disclosure include the steps of immunizing an animal, according to an appropriate immunization schedule with a compound of the present disclosure, such as 5-FU linked to a protein. In some embodiments, 5-FU is coupled to a carrier molecule such as BSA, human serum albumin (HSA), KLH, ovalbumin (OVA), thyroglobulin (TG), tetanus toxin, or synthetic carriers such as multiple antigenic peptides (MAPS). After a suitable time period, antibodies are extracted and/or isolated from the animal. For example, antibodies can be obtained from ascites fluid, blood, or serum, and monoclonal antibodies can be obtained from the fusion of spleen cells with a partner cell line. Antibodies have numerous amino, carboxyl and sulfhydryl groups that might be used for coupling reactions. The Examples section provides exemplary, non-limiting methods for generating some of the antibodies of the present disclosure.

In certain other embodiments, an antibody of the present disclosure can be produced by expressing a heavy and light chain amino acid sequence encoded by SEQ ID NOS: 10 and 11, respectively.

Antibodies

In some embodiments of the present disclosure, a first binding molecule can be an antibody or fragment thereof that binds 5-FU and/or 5-FU conjugated to another molecule(s). For example, the antibody selectively binds to a molecule conjugated to 5-FU as compared to the same molecule without conjugation to 5-FU. When an antibody is described as binding to 5-FU it is understood that this also includes an antibody that selectively binds a molecule conjugated to 5-FU as compared to the same molecule without conjugation to 5-FU.

The antibodies of the present disclosure may be monoclonal or polyclonal antibodies. Depending on the methods of preparation, in certain embodiments, the antibodies of the present disclosure can be in a lyophilized state. Essentially any type of antibody may be used as a binding molecule in accordance with the embodiments of the present disclosure. Suitable examples of such antibodies include, but are not limited to, synthetic antibodies, monoclonal antibodies, recombinantly produced antibodies, intrabodies, multispecific antibodies, bispecific antibodies, human antibodies, humanized antibodies, chimeric antibodies, synthetic antibodies, single-chain Fvs (scFv), Fab fragments, F(ab') fragments, disulfide-linked Fvs (sdFv) and epitope-binding fragments of any of the above. The antibodies used in the present disclosure can include immunoglobulin molecules and portions of immunoglobulin molecules capable of binding the desired binding site. The immunoglobulin molecules of the present disclosure can be essentially of any class or isotype (e.g., IgG, IgE, IgM, IgD, IgA and IgY) or subclass (e.g., IgG1, IgG2, IgG3, IgG4, IgA1 and IgA2) of an immunoglobulin molecule. Camelid antibodies that naturally lack a light chain can also be used. Additionally, structures known as nanobodies and domain antibodies can be used, including polypeptides comprising a single or multiple CDRs of an antibody known to bind the cognate binding site, provided an effective amount of the binding ability is retained.

In certain embodiments, the antibodies of the present disclosure selectively bind 5-FU and/or 5-FU conjugated to another molecule and have one or more of the following characteristics: (i) 3% or less cross-reactivity with uracil in a competitive assay; (ii) less than 3% cross-reactivity with thymine in a competitive assay; (iii) more than 15% cross-reactivity with tegafur in a competitive assay; (iv) less than 1% cross reactivity with one or more compounds selected from the group consisting of capecitabine, uracil, uridine, thymine, thymidine, folinic acid, oxaliplatin, irinotecan, methotrexate and cisplatin; or (v) less than 3% cross reactivity with 5,6-dihydro-5-fluorouracil.

In certain other embodiments, an antibody selectively binds 5-FU and/or 5-FU conjugated to another molecule and has all of the characteristics of (i)-(v). In still other embodiments, an antibody selectively binds 5-FU and/or 5-FU conjugated to another molecule and has both 3% or less cross-reactivity with uracil in a competitive assay and less than 3% cross-reactivity with thymine in a competitive assay.

Some antibodies of the present disclosure can have <2.5%, <2%, <1.5% or <1% cross reactivity with uracil in a competitive assay. In particular, some antibodies can have a cross reactivity with uracil in a competitive assay of 0.81% or less, 1.4% or less, or 2.4% or less. Other antibodies can have <2.5%, <2%, <1.5% or <1% cross reactivity with thymine in a competitive assay. Still other antibodies of the present disclosure can have <2.5%, <2%, <1.5% or <1% cross reactivity with 5,6-dihydro-5-fluorouracil in a competitive assay. Certain antibodies can have >12%, >13%, >15%, >17.5%, >20%, >25% or >30% cross-reactivity with tegafur in a competitive assay.

The present disclosure provides an isolated antibody or fragment thereof that binds 5-FU and/or 5-FU conjugated to another molecule, the antibody comprising a heavy and light chain, wherein the heavy chain amino acid sequence comprises SEQ ID NOs: 3, 4 and 5, and the light chain amino acid sequence comprises SEQ ID NOs: 7, 8 and 9. In certain embodiments, a heavy chain amino acid sequence comprises SEQ ID NO:2 and/or a light chain amino acid sequence comprises SEQ ID NO:6. In some embodiments, a heavy chain amino acid sequence comprises amino acids 20-477 of SEQ ID NO:2 and/or a light chain amino acid sequence comprises amino acids 21-234 of SEQ ID NO:6. In still other embodiments, an antibody or fragment thereof is selected from the group consisting of a monoclonal antibody, a humanized antibody, a chimeric antibody, a single-chain Fv (scFv), an Fab fragment, an F(ab') fragment, and a synthetic antibody.

In some embodiments of the present disclosure, antibodies may have at least one, at least two, at least three, at least four, at least five, or at least six of the CDRs disclosed herein, for example, SEQ ID NOs: 3-5 and 7-9. Certain embodiments of the present disclosure include antibodies that specifically bind to 5-FU and/or 5-FU conjugated to another molecule, wherein the antibody comprises derivatives of the variable heavy (VH) CDRs and/or variable light (VL) CDRs described herein. Standard techniques known to those of skill in the art can be used to introduce mutations (e.g., additions, deletions, and/or substitutions) in the nucleotide sequence encoding an antibody of the invention including, for example, site-directed mutagenesis and PCR-mediated mutagenesis which are routinely used to generate amino acid substitutions. In certain embodiments, the VH and/or VL CDR derivatives can include less than 25 amino acid substitutions, less than 20 amino acid substitutions, less than 15 amino acid substitutions, less than 10 amino acid substitutions, less than 5 amino acid substitutions, less than 4 amino acid substitutions, less than 3 amino acid substitutions, or less than 2 amino acid substitutions as compared to the original VH and/or VL CDRs. Alternatively, mutations can be introduced randomly along all or part of the VH and/or VL CDR coding sequence, such as by saturation mutagenesis, and the resultant mutants can be screened for biological activity to identify mutants that retain activity. Following mutagenesis, the encoded antibody can be expressed and the activity of the antibody can be determined.

The antibodies of the present disclosure can also be produced by immunizing Balb/c mice according to an appropriate immunization schedule (such as that described in the Examples below) followed by injecting the mice with approximately 100 μL to 200 μL of immunogen by intraperitoneal (ip) or intravenous (iv) injection. It is contemplated that other protocols well-known by those skilled in the art may be employed as well. The immunization methods described herein can produce the desired serum antibody response for the 5-FU antibody.

Fusions can then be performed according to standard fusion protocols for creating mouse B cell hybridomas. Hybridomas capable of generating the desired monoclonal antibodies of the present disclosure are obtained by fusing the B cell lymphocytes with an immortal cell line such as myeloma cells. For example, mouse myeloma cells can be fused with spleen cells from mice immunized with the immunogen such as the one described above. Those cells can be seeded until hybridomas appear. The supernatants of the hybridomas can be monitored for immunoglobulin production using known techniques for the desired positive cells which will be used for cloning. The desired clones can then be expanded and the monoclonal antibodies can be harvested according to known procedures.

Three exemplary hybridomas capable of producing cell lines of the 5-FU antibodies were deposited with American Type Culture Collection (A.T.C.C., 10801 University Blvd., Manassas, Va., 20110-2209, USA) on Nov. 12, 2012, with the cell lines being referred to as 36H11, 27F9 and 72B9. The A.T.C.C. accession number for 36H11 is PTA-13314, the accession number for 27F9 is PTA-13313, and the accession number for 72B9 is PTA-13312. Each of the three deposited hybridomas was derived from Balb/c mouse splenic cells fused with a murine myeloma cell line P3X63Ag8.653 (ATCC). These deposits will be maintained under the terms of the Budapest Treaty on the International Recognition of the Deposit of Microorganisms for the Purposes of Patent Procedure.

5-FU Assays

The antibodies described in detail above can be used in the assays of the present disclosure. In certain exemplary embodiments, the present disclosure provides assays capable of detecting and measuring 5-FU in a sample (e.g., plasma or serum) and providing results over a wide dynamic range. Assays of the present disclosure can permit monitoring of 5-FU during infusion and/or after oral administration of 5-FU prodrugs. The present disclosure also provides assays that may be used for identification of patients overexposed to 5-FU due to DPD deficiency or other clearance problems. Additionally, assays of the present disclosure can be used for individualized 5-FU treatment, which can result in improved efficacy and diminished side effects. In some embodiments, the compounds of formula (1) and the antibodies of the present disclosure can be used in the assays provided herein.

Some embodiments of the present disclosure also provide methods of detecting 5-fluorouracil (5-FU) in a sample including the step of (i) combining in a solution at least the sample with a first binding molecule and a detector molecule, wherein the first binding molecule can bind the detector molecule and wherein 5-FU competitively inhibits and/or competes with the binding of the first binding molecule to the detector molecule. The method also includes the step of (ii) detecting the binding of the first binding molecule to the detector molecule. In some embodiments, the method further comprises contacting a sample with a DPD inhibitor. The sample can be contacted with a DPD inhibitor prior to and/or while the sample is incubated with a binding molecule or at any time during the assay.

In some embodiments, the sample can be a serum sample from a mammal, such as a human.

In certain embodiments, the binding molecule can be an antibody, such as those described above. In other embodiments of the present disclosure, a binding molecule (e.g., the first binding molecule) can be from a lyophilized composition and/or a detector molecule can be from a lyophilized composition. In still other embodiments, a binding molecule and a detector molecule can be lyophilized in separate compositions. For example, some assay formats may work better when the sample and binding molecule are combined prior to the addition of a detector molecule or all three are combined at essentially the same time. In certain embodiments, a detector molecule and a binding molecule are not in the same solution unless the sample is present. In some situations it is better to not combine a detector molecule and binding molecule in a solution prior to addition of a sample. In other embodiments, a (first) binding molecule and sample are combined prior to the addition of a detector molecule. For example, a solution comprising a sample and a first binding molecule may be incubated for a period of time prior to the addition of a detector molecule.

In some embodiments of the assays, a lyophilized composition containing a binding molecule or a detector molecule or both is rehydrated with the sample. This embodiment is advantageous in that the sample is essentially not diluted during the assay, which can result in higher levels of sensitivity because more 5-FU is present in an undiluted sample as compared to a diluted sample of the same volume. In some embodiments, a sample is diluted prior to combining with a binding molecule. In some embodiments, a sample is not diluted prior to combining with a binding molecule.

Components/reagents used in exemplary embodiments of the assays of the present disclosure can be lyophilized using standard lyophilizing methods. For example, the components and reagents can be lyophilized by creating a solution containing the desired component(s), such as a detector molecule or binding molecule. Then the solution can be used to form drops that are allowed to fall into a freezing medium (e.g., liquid nitrogen), typically forming frozen spheres, and then lyophilizing the frozen spheres or pellets.

In other exemplary embodiments, a first binding molecule is bound to a surface during an assay or method of the present disclosure. This binding can be performed prior to contacting the first binding molecule with the sample or after. The first binding molecule can be bound to a surface directly (e.g., covalently) or indirectly (e.g., using binding pairs). Examples of suitable binding partners include, but are not limited to, biotin/streptavidin; antibody/antigen; antibody/Fc receptor; an antibody of a first species and an antibody of a second species against first species antibodies; Fc/Fc receptor; polyA/oligodT; 6-His/Ni$^{2+}$; 6-His/cobalt; 6-His/divalent cation resin; complementary DNA strands; lymphotoxin-alpha (LT-alpha)/LT-alpha receptor; lymphotoxin-beta (LT-beta)/LT-beta receptor; T-cell antigen gp39 (CD40L)/CD40; CD30L/CD30; FASL/FAS; 4-1 BBL/4-1 BBL receptor; OX40L/OX40L receptor; and TNF-related apoptosis inducing ligand (TRAIL)/TRAIL receptor. In certain exemplary embodiments, a binding pair that binds binding partners can be streptavidin and biotin or two antibodies that bind each other such as an antibody that binds an Fc portion of another antibody. In other embodiments, a first binding molecule may be bound to a surface through the interaction of numerous binding pairs. In still other embodiments, a binding molecule and a surface can each be a corresponding member of a binding pair. It is contemplated that essentially any method can be used that results in a binding molecule being bound to a surface, e.g., directly or indirectly. In some embodiments, a first binding molecule comprises biotin and a surface comprises streptavidin or vice versa.

In certain exemplary embodiments, an assay or method of the invention can be performed wherein a first binding molecule and sample are incubated for a period of time followed by the first binding molecule being bound to a surface. In other embodiments, a first binding molecule is bound to a surface prior to being contacted with a sample. Some exemplary embodiments of the present disclosure provide a first binding molecule bound to a surface (e.g., a bead) in a lyophilized state.

The sample used in the assays and methods of the present disclosure can be blood plasma or serum from a patient, for example.

Examples of suitable surfaces of the present disclosure include, but are not limited to, a bead, a plate, a glass surface (e.g., a glass slide or bead), a plastic surface, a metal surface, a polystyrene surface (e.g., a bead or a plate), a nitrocellulose surface, or a nano-particle surface. In exemplary embodiments, the bead can be a paramagnetic bead such as those available from Invitrogen, e.g., M270 and M280 related beads.

The detector molecules of the present disclosure can be those that bind a first binding molecule and for which 5-FU competitively inhibits binding of the detector molecule to the first binding molecule. Thus, in certain exemplary embodiments, a detector molecule can have a detectable label, also referred to herein as a detection label. In some embodiments, an assay or method of the present disclosure uses an unlabeled detector molecule and a second binding molecule having a detection label, wherein the second binding molecule binds the detector molecule but does not substantially inhibit or compete for binding of the detector molecule to the first binding molecule. For example, the detector molecule is not directly labeled, but is labeled indirectly as a result of being bound to a second binding molecule having a detection label.

In certain exemplary embodiments of the present disclosure, a detector molecule has the formula:

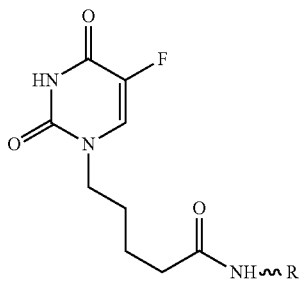

wherein R comprises a protein and/or a detection label. In some embodiments, R can be a protein that is bound to one or more detection labels. In some exemplary embodiments, a detector molecule can be one of the following:

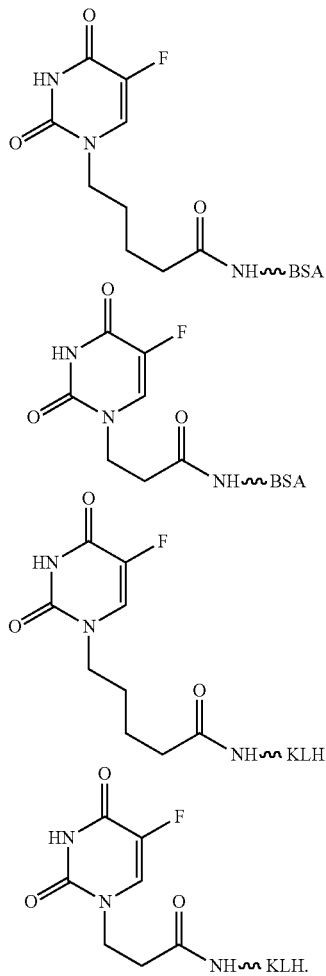

In exemplary embodiments of the present disclosure, one or more detection labels can be attached to the detector molecule, for example, attached to the BSA or KLH protein.

Suitable examples of detector molecules of the present disclosure also include those described below in Example 15.

Advantageously, the antibodies and/or assays of the present disclosure can allow for the detection of very low concentrations of 5-FU. The assays, for example, can have a lower detection limit for 5-FU of <5.0 ng/mL; <10.0 ng/mL; <25.0 ng/mL; <35 ng/mL; <50 ng/mL; <100 ng/mL; <150 ng/mL; or <200 ng/mL in a sample, such as serum or plasma. Some assays of the present disclosure have a dynamic range of 10-30,000 ng/mL.

The present disclosure also provides methods that require a relatively short period of time for detecting 5-FU in a sample. For example, some assays or methods of the present disclosure can detect 5-FU in a sample and can be completed in less than 3, 5, 7, 10, 12, 15, 20, 30, 45 or 60 minutes starting from the time that the binding molecule contacts the sample.

Detection labels that are used in the present disclosure can be those that are compatible with an assay format and include, but are not limited to, an electrochemiluminescence label, an enzymatic label, a fluorophore, a latex particle, a magnetic particle, a radioactive element, a phosphorescent dye, a dye crystalite, a gold particle, a silver colloidal particle, a selenium colloidal particle, a metal chelate, a coenzyme, an electro active group, an oligonucleotide, and a stable radical. Examples of suitable metal chelates include, but are not limited to, ruthenium or osmium metal chelates (e.g., see U.S. Pat. No. 5,310,687). Suitable enzymatic labels include, but are not limited to, horseradish peroxidase and alkaline phosphatase. In some assay formats described herein, "TAG" or "TAG Plus" is used as an exemplary type of detection label. However, it is contemplated that any compatible label type could be used in these assays.

It is further contemplated that the assays of the present disclosure can be performed using any assay type that is compatible with an assay format of the present disclosure such as an electrochemiluminescence (ECL) assay or an enzyme-linked immunosorbent assay (ELISA) assay. ECL assays can be a more stable assay technology and are advantageous as they produce higher sensitivity and have a wider dynamic range (low to high).

An overview of ECL assays is provided in Mathew et al. (Kathmandu University Medical Journal, 2005, 3:91-93) and Forster et al. (Annu Rev Anal Chem. 2009, 2:359-85). ECL can be used for detection. ECL or electro generated chemiluminescence is a form of chemiluminescence in which the light emitting chemiluminescent reaction is preceded by an electrochemical reaction.

Some ECL-based assays of the invention can involve a capture step, which includes the use of a binding molecule (capture agent) that is or can be bound or attached to a surface having an incorporated electrode, and a detection step, which uses a detection molecule coupled directly or indirectly to an ECL label. An ECL label provides light emission generated from a chemiluminescent reaction stimulated by an electrochemical reaction, see, e.g., U.S. Pat. Nos. 5,068,088; 5,093,268; 5,061,445; 5,238,808; 5,147,806; 5,247,243; 5,296,191; 5,310,687; 5,221,605; and 6,673,533. ECL labels are also generally referred to as TAGs. Commonly used ECL labels include, but are not limited to, organometallic compounds, where the metal is from, for example, the noble metals of group VIII, including Ru-containing and Os-containing organometallic compounds such as the Ru(2,2'-bipyridine)32+ moiety (also referred to as "Rubpy" or "TAG1", see, e.g., U.S. Pat. No. 5,238,808). Also, derivatives of TAG1 and Rubpy can be used as ECL labels. ECL-based detection systems use an electrical potential to excite an ECL label to emit light. In some embodiments, a molecule, such as oxalate or tripropylamine, is added during a detection method which promotes the chemical reaction and consequently results in the emission of measurable light from the ECL label.

In certain exemplary embodiments using ECL, a preparation of biotin and/or ruthenium (e.g., BV-TAG Plus or BV TAG) modified protein (e.g., an antibody) conjugates are used and, for example, can be obtained through the modification of primary amine groups ($-NH_2$) using NHS-ester biotin and BV-TAG Plus NHS Ester or BV-TAG NHS Ester. Some ECL analyzers detect light emitted from paramagnetic beads-coupled to ruthenium on its platinum electrode (e.g., inside the flow cell) when a voltage is applied. The light is detected using a photodiode detector and its intensity is proportional to the amount of ruthenium label on the bead surface.

In some embodiments of the present disclosure, a detection method (e.g., an ECL-based method) may include a wash step, for example, after the addition of a binding molecule, after the addition of a sample, or after the addition of a detector molecule. In some embodiments, a wash step is performed after each step of the detection method. In other embodiments, a wash step is performed as the last step prior to detection and in still other embodiments it is the only wash step. A wash step can be used to remove, or wash away any unbound molecules/components such as capture binding molecules, components/molecules of a sample, or labeled detection molecules. A wash step is typically performed using a wash buffer. In some embodiments, a wash buffer includes a surfactant, an acid, a base salt solution or any combination thereof.

Additionally, an assay reagent, such as a buffer (e.g., a sample buffer) and/or wash buffer, may contain additional molecules, such as for example, in a sample buffer containing 100 mM Sodium Phosphate, (pH 7.1); 150 mM Sodium Chloride (NaCl); 0.03% Tween-20; 0.05% Proclin 300; 0.5% Bovine Serum Albumin (BSA); 0.025 mg/mL HRB1; 0.5% Bovine IgG (BGG); 0.05 mg/mL MAK-33 IgG Poly; 15% Trehalose; and 2% PEG.

The samples used in the methods of present disclosure, can be from a patient and the method can further include the step of adjusting a patient's dose of 5-FU based on the amount of 5-FU detected in the sample. For example, it is known or can be determined what range of 5-FU in a patient's serum/blood results in the best treatment outcomes, so that adjustments can be made to the dose given to the patient to optimize treatment.

In some embodiments, the assays or methods include the use of a Gly-Pro-Arg-Pro amide (GPRP-$NH_2$; SEQ ID NO:1). In other embodiments, GPRP-$NH_2$ (SEQ ID NO:1) is used to block the formation of fibrin network, which can interfere with particular assay types or formats, such as those using beads.

Certain exemplary embodiments of the methods or assays of the present disclosure can advantageously detect 5-FU in small sample volumes using small volumes of reagents, and in some cases using a lyophilized first binding molecule and/or detector molecule or both. These features can allow the methods or assays to be used in a point of care setting.

The binding molecules of the present disclosure are molecules that can bind to a desired site and include, but are not limited to, antibodies, peptides, lectins, aptamers and monobodies (also known as ADNECTINS™).

Kits

The present disclosure relates generally to various kits. The kits may include compounds or reagents that can be used in the assay or methods such as a binding molecule and a detector molecule, where the binding molecule can be an antibody. The antibodies can include those described in the present disclosure. The detector molecules can include a detection label, for example, an ECL label. In some embodiments, the binding molecule and/or the detector molecule is in a lyophilized state. In other embodiments, the binding molecule and detector molecule are contained in separately lyophilized compositions.

The present disclosure also relates generally to ECL detection kits for detecting 5-FU in a sample. In some embodiments, a kit includes (i) a binding molecule (e.g., an antibody) optionally immobilized or bound to a surface (e.g., a bead); and (ii) a labeled detector molecule, wherein the binding molecule can bind the detector molecule, and wherein 5-FU competitively inhibits binding of the binding molecule to the detector molecule. In some embodiments, the kit can be used in combination with a portable ECL analyzer. Examples of ECL analyzers which can be used include, but are not limited to, M-SERIES® MIM analyzer (BioVeris, Gaithersburg, Md.) and Meso Scale Discovery's Sector Imager 6000, Sector Imager 2400, Sector PR 400 and Sector PR 100.

It is contemplated that any method or composition described herein can be implemented with respect to any other method or composition described herein. The use of the word "a" or "an" when used in conjunction with the term "comprising" in the claims and/or the specification may mean "one," but it is also consistent with the meaning of "one or more," "at least one," and "one or more than one." The use of the term/phrase "and/or" when used with a list means one or more of the listed items may be utilized, e.g., it is not limited to one or all of the elements.

As used herein the transitional term "comprising" is open-ended. A claim utilizing this term can contain elements in addition to those recited in such claim. Thus, for example, the claims can read on methods that also include other steps not specifically recited therein, as long as the recited elements or their equivalent are present.

Citation or discussion of a reference herein shall not be construed as an admission that such is prior art to the present invention. All publications, patents and patent applications mentioned in this specification are herein incorporated by reference in their entirety into the specification to the same extent as if each individual publication, patent or patent application was specifically and individually indicated to be incorporated herein by reference. Also incorporated by reference is any supplemental information that was published along with any of the aforementioned publications, patents and patent applications. For example, some journal articles are published with supplemental information that is typically available online.

EXAMPLES

The following examples are intended to be non-restrictive and explanatory only.

Whereas, particular embodiments of the invention have been described herein for purposes of description, it will be appreciated by those skilled in the art that numerous variations of the details may be made without departing from the invention as described in the appended claims.

The following materials and equipment were used throughout some or all of the examples described herein:

Bovine Serum Albumin (BSA) (Roche Diagnostics); Tween 20 (Sigma); 2-Methyl-4-isothiazolin-3-one hydrochloride (MIT) (Sigma); Amicon Ultra 30K Filter (15 mL) (Millipore); Slide-A-Lyzer® Dialysis Cassette (Thermo Scientific); Freund's Adjuvant, Incomplete and Complete (Sigma); BV-TAG Plus NHS ester (BioVeris); EZ-Link Sulfo-NHS-LC-Biotin (Thermo Scientific); Dynabeads M280-SA (Invitrogen); Hemocyanin from *Megathura crenulata* (keyhole limpet) KLH (Sigma); Pierce Protein A Plus Agarose (Thermo Science); 5-Fluorouracil (5-FU) and Uracil (Sigma); 5-Fluorodihydropyrimidine-2,4-dione (DH-5-FU) (Medical Isotopes); Ftorafur (Tegafur) (Acros Organics); Dulbecco's Modified Eagle Medium (DMEM) (1X) (Invitrogen); UltraDOMA serum-free hybridoma medium (Lonza); Pierce® Rapid Isotyping Kits—Mouse (Thermo); OPI Media Supplement-Hybri-Max™ (Sigma); Penicillin-Streptomycin Solution Hybri-Max™ (pen/strep) (Sigma); IL-6 Recombinant Mouse (Invitrogen); Fetal Bovine Serum, Ultra-Low IgG (Invitrogen); Fetal Bovine Serum (ATCC); Defined Fetal Bovine Serum (HyClone); L-Glutamine 200 mM (Lonza); L-Glutamine—200 mM (Invitrogen); HT Supplement (100X), liquid (Invitrogen); HAT Supplement (50X), liquid (Invitrogen); HYBRIDOMA CLONING SUPPLEMENT (PAA Laboratories Inc); Dimethyl sulfoxide—Hybri-Max™ (Sigma); Polyethylene Glycol 1500 (Roche Applied Science); Trypan Blue solution—0.4% (Sigma); P3X63Ag8.653 (ATCC); Red Blood Cell Lysing Buffer Hybri-Max™ (Sigma); M384 Analyzer (BioVeris); and M1MR Analyzer (BioVeris).

Example 1

Synthesis of 5-FU Based Immunogen

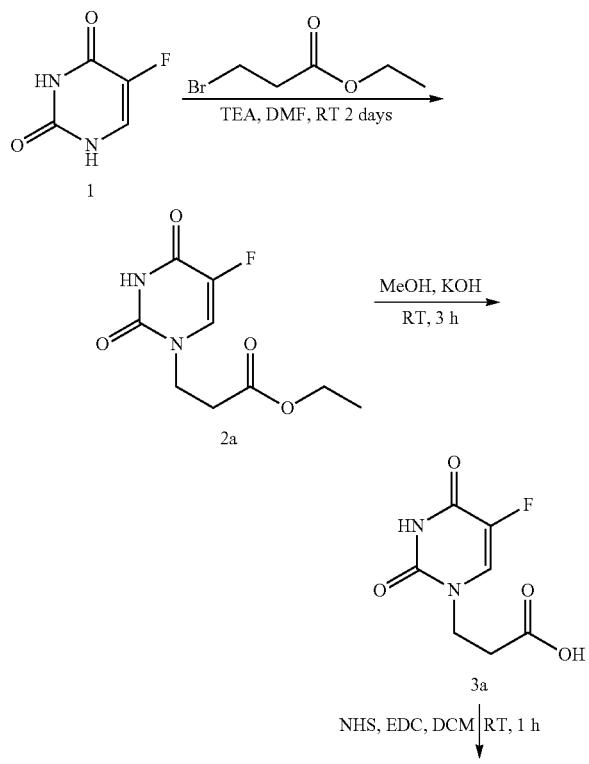

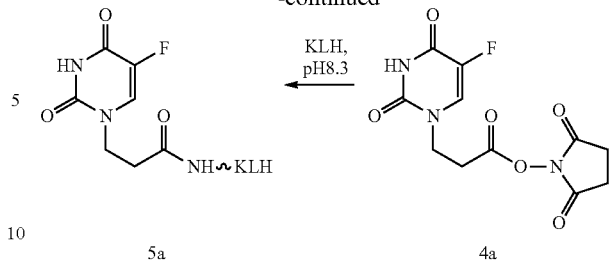

The scheme presented above was used to synthesize one of the exemplary 5-FU-based immunogens of the present disclosure, the steps for which are as follows:

[2a] A solution of 5-Fluorouracil ([1], 1.8 g, Sigma-Aldrich, Cat. #858471-5G) in 16 mL of dimethylformamide (Sigma-Aldrich, Cat#227056-100 mL) was mixed with triethylamine (2.8 g, Sigma-Aldrich, Cat#T0886-1L) and stirred at 30° C. To the above mixture was added dropwise ethyl-3-bromopropionate (2.95 g, Sigma-Aldrich, Cat#128163-25G). The resulting mixture was stirred for 48 hours at room temperature. The solvent was removed under reduced pressure. The residue was taken up with water and extracted with ethyl acetate (3×100 mL). The combined organic layers were dried over sodium sulfate and concentrated. The product was purified by a flash column employing 1-3% methanol in dichloromethane. The desired product was recrystallized from dichloromethane/hexanes to yield 2.3 g of compound.

[3a] To a solution of [2a] (220 mg) in 4 mL of methanol (Sigma-Aldrich, Cat#322415-2L) was added 20% potassium hydroxide (EMD, Cat#PX1480-11) aqueous solution (0.4 mL). The resulting mixture was stirred at room temperature for 12 hours and concentrated. The residue was taken up in 10 mL of water and adjusted to pH 2-3 with 2N HCl solution. The mixture was extracted with ethyl acetate (3×20 mL). The organic phase was combined, dried over sodium sulfate and concentrated to yield 198 mg of compound.

[4a] To a mixture of [3a] (198 mg) and N-hydroxysuccinimide (260 mg, Sigma-Aldrich, Cat#220051-5G) in 20 mL of dichloromethane (Sigma-Aldrich, Cat#270997-1L) was added of 1-ethyl-3-(3-dimethylamino)propyl carbodiimide (900 mg, Sigma-Aldrich, Cat. #E7750-25G). The resulting mixture was stirred for 1.5 hours at room temperature under argon. The resulting mixture was washed with 0.05N HCl (20 mL), water (2×20 mL), dried over sodium sulfate and concentrated to yield 67 mg of compound.

[5a] Modification of Keyhole limpet hemocyanin (KLH) with 1-3C-5-FU-NHS ester. KLH was first concentrated in 15-mL Amicon Ultra 30K filters and buffer exchanged into a phosphate buffered saline containing 10.5 mM KH$_2$PO$_4$, 139.5 mM K$_2$HPO$_4$ and 150.6 mM NaCl, pH 7.7-7.9 (typically pH 7.8). KLH was then modified with 1-3C-5-FU-NHS, which was freshly dissolved in DMSO, at a challenge ratio of 100:1 (molar ratios of 1-3C-5-FU-NHS to KLH, FW=150 kD). After the modification, 1-3C-5-FU-KLH was buffer-exchanged in a dialysis cassette and stored in 1× PBS at −80° C.

Example 2

Immunization of Balb/c Mice (Production of 5-FU Antibodies in Mice Using 1-3C-5-FU-KLH Conjugates)

5-FU immunogens were prepared by emulsifying 1-3C-5-FU-KLH in Complete Freund's Adjuvant (CFA) and Incomplete Freund's Adjuvant (IFA) for primary immunization and booster immunizations, respectively. Emulsions were prepared by mixing antigen and adjuvant on a vortex mixer at its top speed for 15 minutes.

To immunize Balb/c mice, eight mice each received 200 µL of immunogen containing 50 µg protein and CFA in 200 µL for its primary immunization by intra peritoneal (IP) injection and 25 µg protein and IFA in 200 µL for booster immunizations by subcutaneous inoculation at multiple locations on the back. The mice were immunized with 1-3C-5-FU-KLH (Freund's Adjuvant, Complete) with the primary immunization on day 1 as an intraperitoneal (IP) injection. The first through the fourth boosters were administered subcutaneously on days 15, 29, 56, and 83, respectively, when the mice were immunized with 1-3C-5-FU-KLH (Freund's Adjuvant, incomplete).

Example 3

Analysis of Anti-5-FU Antibody Responses in Mice

This Example describes the analysis of serum 5-FU antibody response and antibody specificity to 5-FU and related chemicals.

Serum samples were taken after the 2nd booster immunization and were analyzed at various dilutions in an antibody assay buffer or 5-FU Antibody Screen Buffer containing 1× PBS, 0.5% of BSA, 0.3% Tween® 20 and 0.1% MIT. Serum samples are analyzed by a "bridging assay" where the presence of an anti-5FU antibody creates an immune complex, which contains a Bi-1-3C-5-FU-BSA, 5-FU antibody and TAG Plus-1-3C-5-FU-BSA and is formed by the binding of Bi-3C-5-FU-BSA to one of the binding sites on the anti-5-FU antibody and the binding of TAG Plus-1-3C-5-FU-BSA to the other binding site of the antibody. This immune complex can be captured by the M280-SA bead bound to the Bi-1-3C-5-FU-BSA thereby linking the TAG Plus label to the M280-SA bead.

Diluted samples were tested with 5-FU antibody assay reagent master mix containing 100 ng/mL of Bi-1-3C-5-FU-BSA and 100 ng/mL of TAG Plus 1-3C-5-FU in 200 µg/mL of M280-SA beads. In a typical experiment, serum samples were first diluted in the assay buffer to desired dilutions and 25 µL of the diluted serum samples were mixed with 50 µL of antibody detection master mix and incubated for 30-minutes in a 96-well plate with shaking. After the incubation, M280-SA beads were recovered by attaching a plate magnet (LifeSep™ 96F, Dexter Magnetic Technologies Inc., Elk Grove Village, Ill. 60007) to the plate for >2 min and quickly inverting the plate to remove reaction matrices. Recovered M280-SA beads were resuspended in 150 µL DILUENT which is a PBS-based buffer solution containing 1.8 mM $KH_2PO_4$, 10 mM $Na_2HPO_4$, 120 mM NaCl, 2.7 mM KCl, 0.033% Tween20 and 0.10% KATHON® CG/ICP II (Cat: 48178-U, Sigma, St. Louis, Mo.). The samples were read for ECL signal (ECL counts) either in an M1MR or an M384 ECL analyzer with a 96-well standard protocol with 100 µL draw volume.

Antibody specificities were further analyzed using a competitive antibody assay format. These assays were performed in the presence of 5-FU and other 5-FU structurally related chemicals.

Two mice were selected for hybridoma fusion based on their anti-5-FU serum titer, specificity to 5-FU and cross-reactivity to uracil and 5-Fluorodihydropyrimidine-2,4-dione (DH-5-FU).

Example 4

Immunization of Balb/c Mice (Production of 5-FU Antibodies in Mice Using 1-3C-5-FU-KLH and 1-5C-5-FU-KLH Conjugates)

5-FU immunogens were prepared by emulsifying 5-FU-KLH conjugates 1-3C-5-FU-KLH and 1-5C-5-FU-KLH in Complete Freund's Adjuvant (CFA) and Incomplete Freund's Adjuvant (IFA) for primary immunization and booster immunizations, respectively. Emulsions were prepared by mixing antigen and adjuvant on a vortex mixer at its top speed for 15 minutes or by pushing the mixture through an emulsifying needle for more than 50 times.

5-6 week old female Balb/c mice were typically received 200 µL of immunogen containing 50 µg of protein and CFA in 200 µL for one primary immunization by intra peritoneal (IP) injection and 25 µg protein and IFA in 200 µL for multiple booster immunizations by subcutaneous inoculation at multiple locations on the back. Booster immunizations were typically performed after about 2 weeks post primary immunization and were administered multiple times at 2-6 weeks internal.

To analyze the polyclonal 5-FU antibodies in the mice, multiple serum samples were taken after the 2nd booster immunization and were analyzed at various dilutions in an antibody assay buffer containing 1× PBS, 0.5% of BSA, 0.3% Tween® 20 and 0.1% MIT. To select a mouse developed antibody response with the highest sensitivity for 5-FU, serum samples were analyzed with a variety of antibody detection assays including a typical indirect antibody assay, which detects captured 5-FU specific antibody with a labeled anti-mouse antibody, with ELISA and ECL technology and an ECL-based "bridging assay".

For indirect antibody detection assay with ECL technology, 25 µL of diluted serum samples were first mixed with 25 µL of assay buffer with or without competing chemicals and then with 25 µL of assay buffer containing 5 ng of capture reagent, which were biotinylated position-1-modified 5-FU BSA conjugates with a 3-carbon linker (Bi 1-3C-5-FU BSA) or with a 5-carbon linker (Bi-1-5C-5-FU BSA) pre-bound to 5 µg of paramagnetic M280-streptavidin beads (M280-SA beads) for an incubation of 10 minutes with shaking. After the incubation, M280-SA beads were washed twice with 150 µL of assay buffer. During each wash, beads were recovered by attaching a plate magnet (LifeSep™ 96F, Dexter Magnetic Technologies Inc., Elk Grove Village, Ill. 60007). 5-FU specific antibodies bound to the M280-SA beads were detected with 100 µL of 0.5 µg/mL TAG Plus conjugated goat-anti-mouse IgG, Fey fragment specific antibody (Jackson ImmunoResearch Lab. Cat: 115-005-071) (TAG Plus GAM) in assay buffer for an additional 10 minute incubation. After the incubation, beads were washed once and resuspended in 150 µL DILUENT, which is a PBS-based buffer solution containing 1.8 mM $KH_2PO_4$, 10 mM $Na_2HPO_4$, 120 mM NaCl, 2.7 mM KCl, 0.033% Tween20 and 0.10% KATHON® CG/ICP II (Cat: 48178-U, Sigma, St. Louis, Mo.). The samples were read for ECL signal (ECL counts) either in an M1MR or an M384 ECL analyzer with a 96-well standard protocol with 100 µL draw volume.

The ECL signal in each sample was proportional to 5-FU antibodies bound to the capture reagent bound beads and was inversely proportional to the amount of 5-FU and 5-FU structurally related chemical if the antibody was cross-reactive to the chemical. The 50% inhibitory concentration of 5-FU (5-FU IC50) was defined as the concentration which resulted 50% decrease of the ECL assay. 1050 values were calculated by analyzing the antibody reactivity on serially diluted 5-FU curve in a curve fitting program (SoftMax Pro GxP v5.2, Molecular Devices Inc.). A lower 5-FU IC50 reflected a higher 5-FU antibody sensitivity. Antibody cross-reactivity of a 5-FU structurally related chemical was defined as the percentage ratio of the 1050s of 5-FU and the competing chemical. Table 1 summarizes the 5-FU polyclonal antibody reactivity with 5-FU and the cross-reactivity with tegafur.

Two pooled 5-FU polyclonal antibodies, which consisted of equal portions of serum samples from 5 mice in each group, were selected for their specificity for 5-FU (5-FU IC50) and cross-reactivity with tegafur with this indirect ECL antibody assay. The 5-FU antibodies developed in mice immunized with the 3-carbon linker 5-FU conjugates had a 5-FU IC50 of 12.4 µg/mL, which was substantially lower than the 5-FU 420 µg/mL of antibodies in mice with the 5-carbon 5-FU conjugates. The 3-carbon linker 5-FU conjugate immunized mice also had a much lower cross-reactivity with tegafur (164% vs. 2972%), and were therefore a preferred immunogen for eliciting 5-FU antibody responses.

TABLE 1

5-FU Polyclonal Antibody Reactivity with 5-FU and Cross-reactivity with Tegafur

| Linkers of 5-FU Conjugates Modified at Position 1 | IC50 (ng/mL) with 5-FU | Cross-reactivity with Tegafur |
| --- | --- | --- |
| 3-Carbon Linker | 12,402 | 164% |
| 5-Carbon Linker | 420,138 | 2972% |

Antibody responses were also analyzed with a "Bridging Assay", which was a more rapid and convenient assay for antibody detection. Typically, diluted samples were tested with 5-FU antibody assay reagent master mix containing 100 ng/mL of Bi-1-3C-5-FU-BSA and 100 ng/mL of TAG Plus 1-3C-5-FU in 200 µg/mL of M280-SA beads. In a typical experiment, serum samples were first diluted in the assay buffer to desired dilutions and 25 µL of the diluted serum samples were mixed with 50 µL of antibody detection master mix and incubated for 30-minutes in a 96-well plate with shaking. After the incubation, M280-SA beads were recovered by attaching a plate magnet (LifeSep™ 96F, Dexter Magnetic Technologies Inc., Elk Grove Village, Ill. 60007) to the plate for less than 2 min. and quickly inverting the plate to remove reaction matrices. Recovered M280-SA beads were resuspended in 150 µL DILUENT.

Example 5

Creation, Screening and Isotyping of 5-FU Antibody Producing Hybridomas

To prepare the tissue culture media, OPI Media Supplement-Hybri-Max™, contents of a vial with 10 mL sterile water (0.2 um filtered H2O) for 1 liter of DMEM were reconstituted. For the preparation of murine IL-6 (mIL-6), diluted stocks were prepared in DMEM to a concentration of 100 ng/mL and were kept at 80° C. The final concentration of mIL-6 was 10 µg/mL. To make 500 mL of "Basic Tissue Culture Media" 390 mL DMEM, 5 mL OPI, 5 mL Pen/Strep, 50 µL mIL-6 (100 ng/mL) and 50 mL FBS were mixed and filtered through a 0.2 µm filter. HT Media was the Basic Tissue Culture Media supplemented with 1× HT. HAT Media was the Basic Tissue Culture Media supplemented with 2× HAT and 20% of Hybridoma Cloning Supplement. The cell freezing media was prepared from FBS supplemented with 10% dimethyl sulfoxide (DMSO).

In preparation of the fusion partner, P3×63Ag8.653 cells were grown to <1×10$^6$ cells/mL to obtain about 100 million cells. Cells were pelleted in multiple 50 mL tubes by centrifugation at 200 g for 3 minutes. Cells were washed in 50 mL conical tubes 3 times with 20 mL of pre-warmed DMEM media.

A selected mouse spleen was harvested and stored in 10 mL of ice-cold DMEM. The spleen tissue was teased open and ground in 100 mm petri dish containing 1-2 mL of ice-cold DMEM with the flat end of a sterile syringe plunger. The DMEM with splenocyte suspension was filtered through a 70 µm cell strainer. Splenocytes were pelleted by centrifugation at 400 g for 5 minutes. The pellets were loosened and red blood cells (RBCs) were lysed with 1 mL of RBC lysis buffer for 1 minute. 14 mL of ice-cold DMEM was added. Cells were harvested at 400 g for 5 minutes. 10 mL of DMEM was added to each tube to target a concentration of about 10×10$^6$ cells/mL. Cells were counted under a microscope by mixing 15 µL of cells suspension in 30 µL of DMEM and 15 µL of 0.4% Trypan Blue (final dilution=1:4) and counted under a microscope.

Splenocytes and P3X63Ag8.653 cells were mixed in 50 mL conical tubes at ratios of 1:3 to 3:1 in DMEM media and centrifuged at 400 g for 5 minutes. The supernatant was removed without disturbing the cell pellet. The cell pellets were loosened by gently tapping and swirling the tube. 1.0 ml of 37° C. PEG 1500 was added drop-wise over 1.0 minute while gently stirring with a pipette. After the PEG was added the cap was placed on the tub which was gently swirled for 1.0 min. 15 mL of DMEM was slowly added drop-wise to the tube in gentle drops over 5 minutes and the cells were then incubated for 5 minutes in a 37° C. water bath. 30 mL of warm Basic Tissue Culture Media was slowly added to the tube in gentle drops followed by incubation for 15 minutes in a 37° C. water bath. The cell fusion suspension was centrifuged at 400 g for 5 minutes. Supernatant was removed and the cell pellet was gently resuspended in 50 mL Basic Tissue Culture Media. 50 µL of cell suspension was transferred to each well of a 96 well plate and then placed in a 37° C., 5% CO$_2$ tissue culture incubator overnight. The next day 50 µL of 2×HAT medium was added to each well and then the plates were returned to the tissue culture incubator. To each well, 50 µL of 1× HAT media was added at days 3 and 7 and 100 µL of 1× HT media was added at days 9 to 11. If necessary certain volumes of media in each well were removed before freshly media were added.

Hybridomas were screened between days 10-14 for the secretion of 5-FU antibody by the 5-FU antibody assay (Bridging-assay) described before. 25 µL of culture supernatant were transferred to an assay plate and mixed with 50 µL of 5-FU antibody assay master mix containing 100 ng/mL of each Bi-1-3C-5-FU-BSA and TAG Plus 1-3C-5-FU-BSA in 200 µg/mL of M280-SA beads. Samples were incubated for 30 minutes with shaking. Beads were recovered and resuspended in 150 µL of DILUENT and read in an M384 analyzer with 100 µL draw volume. Hybridomas identified from plates with greater than 20% of growing wells were re-cloned by limiting dilution in 96-well plate at 0.3 and 1.0 cells/well.

5-FU antibody specificity and cross-reactivity was tested on hybridomas that were identified as positive for 5-FU binding. Hybridoma culture supernatants were tested for antibody specificity and cross-reactivity by competition assays in the presence of 5-FU and other structurally similar chemicals including uracil, DH-5-FU and tegafur. In some experiments, hybridoma culture supernatants were tested at 1:5 serial dilutions to determine the optimal concentration for the subsequent competition testing.

Typically, 25 µL of culture supernatant were mixed with 50 µL of 5-FU assay master mix containing 100 ng/mL of each Bi-1-3C-5-FU-BSA and TAG Plus 1-3C-5-FU-BSA in 200 µg/mL of M280-SA beads with or without competing chemicals. Samples were incubated for 30 minutes. Beads were recovered and resuspended in 150 µL of DILUENT and read in an M384 analyzer with 100 µL draw volume.

X_RCT=cross-reactivity (calculated 5-FU concentration/10 µg/mL). Hybridomas 26H7, 27F4, 27F9, 36H11, 49D8, 61C6 and 72B9 showed better specificity to 5-FU (signal decreased in the presence of low level of 5-FU) and were selected for expansion and cloning by limiting dilution.

The antibody isotypes were determined with Pierce Rapid Antibody Isotyping Kit plus Kappa and Lambda—Mouse (Thermo Fisher Scientific). The isotypes and the light chain for hybridoma cell lines 26H7 and 27F4 could not bet determined. The isotypes for the 27F9, 36H11, 49D8 and 72B9 hybridomas were determined to be IgG1 and all had the κ light chain. The isotype for 61C6 was IgG2b with the κ light chain.

Example 6

Creation and Screening of 5-FU Antibody Producing Hybridomas

Fusions were performed according to a general fusion protocol for creating mouse B cell hybridomas. A mouse spleen from a selected responder was harvested and stored in 10 mL of ice-cold DMEM. Fused murine B-cells were prepared by mixing isolated splenocytes and P3X63Ag8.653 cells at ratios of 1:3 to 3:1 in a plain DMEM media and culture in the DMEM media containing 1% OPI, 1% Pen/Strep, 10 µg/mL of murine rIL-6 and 10% FBS with 1× of HAT for 7-10 days. The cultures were fed with the same DMEM media with 1× HT. Hybridomas were usually screened between days 10-14 for the secretion of 5-FU antibody by the 5-FU antibody assay (Bridging Assay) previously described. Positive hybridomas were typically identified with a signal background of more than 10 with the antibody assay, characterized, and then were isolated from plates with greater than 20% of growing wells in limiting dilution plates at 0.3 and 1.0 cells/well. Positive growing wells were expanded and culture supernatants were harvested for antibody characterization.

Example 7

Analysis of Monoclonal 5-FU Antibodies Derived from Mice Immunized with 5-FU Conjugates with the 3-Carbon Linker Vs. the 5-Carbon Linker with an Indirect ELISA Assay In this experiment, antibody capture reagents were 5-FU BSA conjugates modified at the 5-FU position 1 with either 3-carbon or 5-carbon linkers. 5-FU was conjugated to BSA by mixing 1-5C-5-FU-NHS ester with BSA at a challenge ratio of 12:1 (molar ratios of 1-5C-5-FU-NHS to BSA) in a phosphate buffer containing a phosphate buffered saline containing 10.5 mM $KH_2PO_4$, 139.5 mM $K_2HPO_4$ and 150.6 mM NaCl, =pH 7.7-7.9 (typically pH 7.8) for 1 hour or more incubation at room temperature (typically 1 hour incubation at room temperature). After the incubation, unbound 1-5C-5-FU-NHS ester was removed by 3 buffer exchanges in an AmiconUltra4-30K filter (Millipore, Cat#UFC803024). BSA conjugated with 5-FU (5-FU-BSA) was concentrated and stored in the same phosphate buffer (pH 7.8).

This indirect antibody ELISA assay 5-FU assay was constructed using either 1-3C-5-FU-BSA or 1-5C-5-FU-BSA as antibody capture reagent and a horseradish perioxidase (HRP) conjugated goat anti-mouse antibody as the antibody detector reagent. The binding of 5-FU antibody was detected with 3,3,5,5-TetraMethylBenzidine (TMB) as the HRP enzyme substrate. The 5-FU ELISA assay signal ($OD_{450}$) decreased proportionally to the increasing concentration of 5-FU. The 5-FU IC50 and tegafur cross-reactivity were determined as in the previous section.

Monoclonal 5-FU antibodies were obtained from mice immunized with 5-FU conjugates with 3-carbon linker conjugate and with 5-carbon linker conjugate, respectively. Monoclonal antibodies were screened for their highest 5-FU sensitivity (e.g., lowest 5-FU IC50). Selected monoclonal antibody specificities with 5-FU and cross-reactivity with tegafur in mice immunized with 3-carbon and 5-carbon linker conjugates were summarized in Table 2.

Monoclonal antibodies from mice immunized with the 3-carbon 5-FU conjugates showed a substantially lower 5-FU IC50. Notably antibody clones 36H11 and 61C6 had an extraordinarily low 5-FU IC50 at about 56-57 ng/mL and were detected with a tegafur cross-reactivity of 7.6% and 28%, respectively.

The results presented in Table 1 and Table 2 demonstrated that the position 1 modified 5-FU conjugate with a 3-carbon linker, which was a shorter linker, rather than the 5-carbon linker was a preferred immunogen for producing assay antibodies specific for 5-FU. This 5-FU conjugate produced antibodies highly sensitive for 5-FU and with low cross-reactivity for tegafur (12% or lower).

TABLE 2

5-FU Reactivity and Cross-reactivity to Tegafur of Monoclonal Antibodies Generated in Mice Immunized with 5-FU Haptens with 3 Carbon linker vs 5-Carbon Linker.

| 5-FU mAb Clone | 5-FU Immunogen | Plate Coating 5-FU Conjugate | 5-FU IC50* (ng/mL) | Tegafur Cross-reactivity** |
|---|---|---|---|---|
| 26H7 | 1-Substituted 5-FU Conjugated KLH with a 3-carbon Linker | 1-Substituted 5-FU Conjugated BSA with a 3-carbon Linker | 2,303 | 41% |
| 27F9 | | | 7,370 | 30% |
| 36H11 | | | 56 | 7.6% |
| 61C6 | | | 57 | 28% |
| 72B9 | | | 4,082 | 16% |
| 1B10 | 1-Substituted 5-FU Conjugated KLH with a 5-carbon Linker | 1-Substituted 5-FU Conjugated BSA with a 3-carbon Linker | 32,741 | 2400% |
| 3H10 | | | 69,741 | 5895% |
| 11A7 | | | 27,928 | 991% |
| 12E11 | | | 292,035 | 6625% |

*IC50: concentration of an inhbitor at which produces 50% of total esponse
**Cross-reactivity = (IC50 for 5-FU/IC50 for Testing Chemical)%

In addition to tegafur, several 5-FU structurally related chemicals were also evaluated for their cross-reactivity to the antibodies generated with 5-FU conjugate with the 3-carbon linker and were summarized below in Table 3. Most antibodies were not significantly cross-reactive (e.g., with <10% cross-reactivity) with DH-5-FU, uracil, cytosine and thymine except with tegafur. However, antibody 36H11 was highly specific for 5-FU and was detected for about 12% or lower cross-reactivity with tegafur.

TABLE 3

5-FU Monoclonal Antibody Cross-reactivity

| 5-FU mAb Clone | Cross-reactivity | | | | | |
|---|---|---|---|---|---|---|
| | 5-FU | Tegafur | DH-5-FU | Uracil | Cytosine | Thymine |
| 61C6 | 100% | 28% | 1.4% | 1.4% | 0.57% | Undetectble |
| 36H11 | 100% | 7.6% | 0.41% | 0.81% | 0.11% | Undetectble |
| 26H7 | 100% | 41% | 2.5% | 3.6% | Undetectble | 42% |
| 27F9 | 100% | 30% | <2.4% | <2.4% | Undetectble | 6.7% |
| 49D8 | 100% | 13% | <2.4% | <2.4% | Undetectble | 3.6% |
| 72B9 | 100% | 16% | 2.1% | <2.4% | Undetectble | 1.3% |

Cross-reactivity = (IC50 for 5-FU/IC50 for Testing Chemical)%

Example 8

Modulating 5-FU Assay Sensitivity and Dynamic Range by Selecting the Linker Length of 5-FU Conjugate 5-FU antibodies generated with one 5-FU conjugate are typically reactive with a different 5-FU conjugate with a different linker to a various degree. One 5-FU antibody may have a higher or lower sensitivity for a different 5-FU conjugate. 5-FU antibodies usually have higher assay sensitivity with a 5-FU conjugate with a shorter linker and may be more desired for the detection of a more diluted sample. Conversely, a 5-FU conjugate with a longer linker may be more suitable for detecting higher 5-FU concentrations, e.g., with an undiluted sample. The various 5-FU reactivity of a panel of 5-FU antibodies was determined by an indirect ELISA and were summarized in Table 4.

TABLE 4

5-FU mAb Assay Sensitivity on 5-FU Conjugates with 5-Carbon Linker vs 3-Carbon Linker

| 5-FU mAb Clone | Ratio of IC50 on 5-FU Conjugates with 5-carbon Linker vs. 3-carbon Linker |
|---|---|
| 1B10 | 3.2 |
| 11A7 | 4.0 |
| 26H7 | 2.9 |
| 27F9 | 1.7 |
| 36H11 | 4.8 |
| 49D8 | 0.4 |
| 61C6 | 4.7 |
| 72B9 | 2.7 |

All monoclonal antibodies exhibited higher 5-FU IC50 ranging from 1.7 to 4.8 fold increase with a longer linker (5-carbon) except the clone 49D8, which had a lower 1050 with the 5-carbon linker. Nevertheless, 5-FU assay sensitivity and dynamic range can be adjusted by choosing linkers with various lengths.

Example 9

Testing of Antibody 61C6 for 5-FU Detection by ECL Assay

5-FU antibodies were evaluated as assay capture and detector reagents in an ECL assay based on the performance of 5-FU curves prepared in a 5-FU Antibody Screen Buffer and human lithium heparin plasma. Calibrator curves were prepared using charcoal stripped human plasma in Li-heparin. All the purified antibodies were conjugated with TAG Plus NHS ester at a challenge ratio of 15:1 and with EZ-Link Sulfo-NHS-LC-Biotin at a challenge ratio of 10:1.

In addition to evaluating the capture reagent with Biotinylated 5-FU BSA prebound M280-SA beads, this experiment also evaluated 5-FU covalently conjugated to the M270-amine beads as the capture reagent.

Unless otherwise specifically mentioned, a 5-FU immunoassay was set up by mixing the same volumes of sample with capture reagent first and then with detector reagent in a 96 well plate. After adding reagents, samples were mixed for 5 minutes at room temperature with shaking. After the incubation, beads were recovered by attaching a plate magnet to the assay plate for 2 minutes and resuspending in 150 µL of DILUENT. Samples were either read in an M384 or an M1MR analyzer with 100 µL draw volume under the 96 standard round plate protocol.

The performance of TAG Plus conjugated antibody 61C6 as an assay detector reagent was studied. Assay performance was evaluated in 5-FU Antibody Screening Buffer with a 5-fold 5-FU serial dilution curve from 150 µg/mL to 9.6 ng/mL as 5-FU calibrators (samples).

A total of 5 capture reagents were evaluated in this experiment. Three capture reagents were 5-FU bound to M280-SA beads through biotinylated BSA including Bi-1-3C-5-FU-BSA, Bi-1-5C-5-FU-BSA and Bi-3-5C-5-FU-HSA pre-bound to M280-SA beads at the ratio of 1.0 µg capture reagent per mg beads (200 µg/mL). Two other capture reagents were 1-5C-5-FU-M270 and 1-3C-5-FU-M270 for which 5-FU was directly conjugated to M270 amine beads in the buffer to a final concentration of 200 µg/mL.

The assay detector reagent used was TAG Plus 5-FU mAb 61C6 at the concentration of 2.0 µg/mL. The assay was performed as follows: 25 µL of capture reagent were added to each well. 25 µL of 5-FU calibrators (samples) were added to each well and mixed briefly with the capture reagent. 25 µL of detector reagent was added to mixed sample and capture reagent. The plate was incubated for 5 minutes with shaking in a MicroMix 5 Shaker at Form 8 and Amp 6. The beads were recovered and resuspended in 150 µL DILUENT. The plate was read in an M384 ECL Analyzer with a draw volume of 100 µL under 96 standard plate protocol.

The same 5-FU calibrator curve was tested with each capture reagent paired with TAG Plus conjugated antibodies as the capture reagent. Two assay plates were setup for the TAG Plus conjugated 61C6 antibody as a detector antibody with each 5-FU assay capture reagent.

The mean signals and % TB (percentage of total binding=signal with a 5-FU concentration/signal in buffer) of each calibrator curve (e.g., with either pre-bound beads or conjugated M270 beads) were evaluated. The results showed an elevated % TB at 9.6 and 48 ng/mL of 5-FU with the antibody mAb 61C6 with the Bi-1-5C-5-FU-BSA pre-bound M280-SA beads as the capture reagent was likely due to an excess amount of detector antibody which resulted in higher signals exceeding the limit of the ECL Analyzer M384.

One of the experiments used 3-5C-5-FU-HSA as a capture reagent, which is a 5-FU derivative modified at position 3 rather that position 1. Yet the 61C6 antibody was reactive to this 3 position modified 5-FU. The other antibodies selected in Example 5 also were reactive with 3-5C-5-FU-HSA to various levels.

Some calibrators exhibited increased % TB with mAb 61C6 in the experiment with 1-5C-5-FU-M270, which was likely due to the antibody concentration exceeding its optimal concentration.

Antibody 61C6 consistently demonstrated sufficient assay sensitivity with both position-1 modified 5-FU derivatives and position-3 modified 5-FU derivatives as assay capture reagents.

Example 10

Assay Performance of mAb 61C6

This Example describes an evaluation of assay performance with mAb 61C6. The assay performance was evaluated in pooled-human lithium heparin plasma (plasma). Calibrator curves were prepared using charcoal stripped human plasma in Li-heparin. 5-FU calibrator curves were 5-fold 5-FU serial dilution curves in the plasma from 150 µg/mL to 9.6 ng/mL. Testing chemicals were spiked in the plasma to a final concentration of 10 µg/mL. The capture reagent was 1-5C-5FU-M270 beads resuspended in 5-FU Antibody Screen Buffer to a final concentration of 200 µg/mL (25 µL/well). The detector reagent was TAG Plus mAb 61C6 (0.5 µg/mL) in 5-FU Antibody Screen Buffer.

25 µL of capture reagent were added to each well. 25 µL of samples, 5-FU calibrators or competing chemicals, were added to each well and mixed briefly with the capture reagent. 25 µL of detector reagent were added to the mixed sample and capture reagent. The plate was incubated for 5 minutes with shaking on a MicroMix5 shaker. The plate was read in an M1MR Analyzer with a draw volume of 100 µL under 96 standard plate protocol.

Data were analyzed with the SoftMax Pro data analysis software package with a built-in 5-parameter curve fitting algorithm program. The calibrator % TB was the ratio of calibrator signal divided by Cal1 (0.0 ng/mL 5-FU) signal (assay background). The low detection limit (LDL) was the 5-FU concentration of the mean signal of 24 Cal1 replicates minus 2× standard deviation of the 24 Cal1 replicates. The LDL was determined to be 2.7 ng/mL.

Example 11

Cross-Reactivity of Antibody 61C6 to Chemicals Structurally Similar to 5-FU and to Selected Chemotherapy Drugs in the Presence and Absence of 5-FU Cross-reactivity of mAb 61C1 to chemicals and chemotherapy drugs was tested in human plasma in the absence of 5-FU and in the presence of 5-FU at a targeted 400 ng/mL. Cross-reactivity to structurally similar chemicals and chemotherapy drugs was tested at 10 µg/mL and 100 µg/mL, respectively.

Clinical and Laboratory Standard Institute recommends that the "Cross-reactivity of an interferent should be tested both in the absence and in the presence of analyte at a concentration near the upper limit of the therapeutic range" (page 72 of EP07A2).

Calculation of cross-reactivity is shown in the following equation:

% Cross-reactivity=100×(Measured Value−True Value)÷(Concentration of Interferent)

The following are assay reagents used in some of the Examples. Capture reagent: 250 µg/mL 1-5C-5-FU-M270 in Antibody DILUENT, containing 100 mM Sodium Phosphate (pH 7.2), 150 mM Sodium Chloride (NaCl), 0.5% Bovine Serum Albumin (BSA), 0.5% Bovine IgG (BGG), 0.1% 2-Methyl-4-isothiazolin-3-one hydrochloride (MIT), 0.33% Brij-35, 0.05 mg/mL MAK-33 IgG Poly (Roche Diagnostics), 0.025 mg/mL Heterophilic Blocking Reagent-1 (HRB-1, Scantibodies Laboratory, Inc. Santee, Calif. 92071) (30 µL/well). Detector reagent: 1.5 µg/mL TAG Plus mAb61C6 in Antibody DILUENT (30 µL/well). The 5-FU calibrator curve was a 1:5 serial dilution of 5-FU in charcoal stripped human plasma in lithium-heparin ranging from 9.6 ng/mL to 150 µg/mL.

Assay samples where chemicals and chemotherapy drugs at 10 and 100 µg/mL, respectively, were spiked into the same human plasma without 5-FU and with 5-FU (400 ng/mL target concentration).

The chemicals and chemotherapy drugs tested for cross-reactivity included the following: 1.0 mg/mL Tegafur (Teg) in DMSO; 1.0 mg/mL Capecitabine (Cap) in DMSO; 1.0 mg/mL Uracil (Urc) DMSO; 1.0 mg/mL DH5FU in DMSO; 1.0 mg/mL Uridine (Urd) $H_2O$; 1.0 mg/mL Thymine in $H_2O$; 1.0 mg/mL Thymindine (Thymd) $H_2O$; 10 mg/mL Folinic Acid (FolA) $H_2O$; 10 mg/mL Oxaliplatin (Oxp) $H_2O$; 10 mg/mL Irinotecan (IQ) DMSO; 10 mg/mL Methotrexate (Mtx) DMSO; and 10 mg/mL Cisplatin (Csp) DMSO.

30 µL of assay samples and 5-FU calibrators were added to the plate followed with 30 µL of capture reagent. The plate was incubated for 60 seconds with shaking on a MicroMix 5 Shaker at Form 8 and Amp 6 before adding 30 µL of detector reagent. The plate was incubated for 6 minutes with shaking on a MicroMix 5 Shaker at Form 8 and Amp 6. The beads were recovered and resuspended in 150 µL DILUENT. The plate was read in an M1MR Analyzer with a draw volume of 100 µL under the protocol for 96 standard plate.

TABLE 5

Cross-reactivity with Antibody mAb 61C6

| | | Without 5-FU | | With 5-FU (379 ng/mL) | |
|---|---|---|---|---|---|
| Chemicals/Drugs | Tested Concentration | Measured Value | Cross-Reactivity (%) | Measured Value | Cross-Reactivity (%) |
| Tegafur | 10 µg/mL | 1624 | 16.2 | 1927 | 15.5 |
| Capecitabine | 10 µg/mL | 0.00 | 0.00 | 366 | −0.13 |
| Uracil | 10 µg/mL | 94.0 | 0.94 | 390 | 0.11 |
| DH5FU | 10 µg/mL | 262 | 2.62 | 553 | 1.74 |
| Uridine | 10 µg/mL | 21.0 | 0.21 | 395 | 0.16 |
| Thymine | 10 µg/mL | 59.0 | 0.59 | 459 | 0.80 |
| Thymidine | 10 µg/mL | 5.00 | 0.05 | 392 | 0.13 |
| Folinic Acid | 100 µg/mL | 0.00 | 0.000 | 368 | −0.01 |
| Oxaliplatin | 100 µg/mL | 0.00 | 0.000 | 385 | 0.01 |
| Irinotecan | 100 µg/mL | 0.00 | 0.000 | 363 | −0.02 |
| Methotrexate | 100 µg/mL | 0.00 | 0.000 | 357 | −0.02 |
| Cisplatin | 100 µg/mL | 0.90 | 0.001 | 340 | −0.04 |

The cross-reactivity to tegafur, uracil, DH-5-FU and capecitabline determined in this experiment with and without 5-FU was comparable to the results in Example 5. The cross-reactivity to uridine, thymine and thymidine were less than 1.0% with and without 5-FU. The cross-reactivity to chemotherapy drugs at 100 μg/mL including folinic acid, oxaliplatin, irinotecan, methotrexate and cisplatin were essentially undetectable with and without 5-FU. The cross reactivity to tegafur is inconsequential in that the assay will be used primarily to detect 5-FU in samples that will not contain tegafur. For example, the assay will be used to test for 5-FU in samples from patients that did not receive administration of tegafur.

The cross-reactivity profile for antibody 61C6 to the tested chemicals and chemotherapy drugs is acceptable for a 5-FU detection assay.

Example 12

Evaluation of 5-FU Assay Formats, Sample Mixing Sequences, Assay Incubation Timing and Assay Reagent Concentrations In this example, 5-FU assays were setup with various assay samples, capture and detector reagent volumes including 25, 30, 40 and 50μL, but sample, capture and detector reagent volumes were kept the same within one experiment. After assay incubation, beads were recovered by attaching a plate magnet to the assay plate for 2 minutes and resuspending in 150 μL of DILUENT. Samples were either read in an M384 Analyzer or an M1MR Analyzer with 100 μL draw volume of a 96 standard round plate protocol.

5-FU Assay Performance with TAG Plus Conjugated 5-FU-BSA and TAG Plus-5-FU as Assay Detector Reagent and mAb 61C6 as Assay Capture Reagent was evaluated as follows: 5-FU calibrator curves were 5-fold serial dilution curves prepared in human lithium heparin plasma from 150 μg/mL to 9.6 ng/mL. Calibrator curves were prepared using charcoal stripped human plasma in Li-heparin. The capture reagent was Bi-mAb 61C6 prebound M280-SA beads (5.0 μg of antibody per mg of M280-SA beads) resuspended in 5-FU Antibody Screen Buffer to a final concentration of 125 μg/mL (30 μL/well). Detector reagents tested were TAG Plus 1-5C-5-FU, TAG Plus 1-5C-5-FU-BSA and TAG Plus 1-3C-5-FU-BSA.

30 μL of samples were added to each well and mixed briefly with 30 μL of capture reagent. 30 μL of detector reagent were added to the mixed sample and capture reagent. The plate was incubated for 5 minutes with shaking in a MicroMix 5 Shaker at Form 8 and Amp 6. The beads were recovered and resuspended in 150 μL DILUENT. The plate was read in an M384 ECL Analyzer with a draw volume of 100 μL under the protocol for 96 standard plate.

The assay was performed with increasing concentrations of TAG Plus conjugated 5-FU-BSA with 3 carbon and 5 carbon ethyl chain linkers.

The effective 5-FU detection range using TAG Plus 1-3C-5-FU BSA as the detector reagent was approximately 9.6 to 30,000 ng/mL. The % TB at 9.6 ng/mL of 5-FU, was 70%, 75% and 78% at 0.5, 0.75 and 1.0 μg/mL of TAG Plus 1-3C-5-FU-BSA, respectively, suggesting that a lower concentration of detector has a higher sensitivity.

The overall assay performance with TAG Plus 1-5C-5-FU BSA was similar to that of TAG Plus 1-3C-5-FU BSA. The % TB at 9.6 ng/mL of 5-FU, was 82%, 87% and 88% at 0.5, 0.75 and 1.0 μg/mL of TAG Plus 1-5C-5-FU-BSA, respectively, suggesting that lower a concentration of detector has a higher assay sensitivity.

The overall assay sensitivity with TAG Plus 1-5C-5-FU (a 5-FU derivative conjugated to TAG Plus directly through a 5 carbon linker) was lower than the assays with TAG Plus 1-5C-5-FU BSA and TAG Plus 1-3C-5-FU BSA. Lower concentrations of TAG Plus 1-5C-5-FU at 0.050 and 0.10 μg/mL were more sensitive in detecting 5-FU. This assay detector reagent was able to detect 5-FU at 48 ng/mL. Otherwise, the TAG Plus 1-3C-5-FU BSA showed the more favorable results that a lower concentration of detector has a higher assay sensitivity.

It was effective to detect 5-FU using mAb 61C6 as the assay capture reagent and 5-FU conjugated with TAG Plus, either directly or through a carrier protein, as the detector reagent. Similar assay performances were obtained using the antibody 61C6 as the capture reagent and using the mAb 61C6 as the detector reagent.

Example 13

5-FU Assay Detector Incubation Timing

Assay signals were shown to be slightly decreased when the first assay incubation timing was extended from 1 min to 4 min. This experiment evaluated the second assay incubation timing from 3 to 15 minutes.

The 5-FU calibrators included 5-FU spiked in pooled-human lithium heparin plasma (40 μL/well). Calibrator curves were prepared using charcoal stripped human plasma in Li-heparin. The capture reagent used was Bi 1-5C-5-FU BSA prebound (2.0 μg of Bi 1-5C-5-FU BSA per mg of M280-SA beads) resuspended in Antibody Diluent to a final concentration of 125 μg/mL (40 μL/well). The detector reagent used was 0.5 μg/mL of TAG Plus 61C6 in Antibody Diluent (40 μL/well).

Capture reagent was first mixed with 5-FU calibrators and incubated for 30 seconds with shaking (first incubation). After the first incubation, detector reagent was added to the mixture and incubated for an additional incubation from 3 to 15 minutes (second incubation). After the incubation, beads were washed twice in 120 μL of DILUENT and resuspended in 120 μL of DILUENT. The plate was read in an M1MR Analyzer with a draw volume of 70 μL under the protocol for 96 standard plate.

The results showed that the assay signal increased as the second incubation time increased with the exception of one of the calibrators (Cal8 at 150,000 5-FU ng/mL). The percent of total binding in buffer without 5-FU (% TB) did not seem to be affected by the longer incubation time indicating that 3 minutes incubation is sufficient for a 5-FU assay.

Example 14

Summary of Testing Various Parameters of 5-FU Assay

Assay signal increased proportionally with detector antibody concentration from 0.5-1.2 μg/mL. The results demonstrated that 5-FU analyte is stable in Antibody Screen Buffer and in Human Li-Heparin Plasma for at least 4 hours on ice and that 5-FU detector TAG Plus mAb 61C6 is stable in the Antibody Diluent for at least 4 days at 2-8° C.

The capture reagent 1-5C-5-FU-M270 beads appeared to be stable at 2-8° C. for at least 40 hours. The results from the study of the 5-FU assay performance with antibody 61C6, were obtained in less than 7 minutes, and showed that the 5-FU assay with antibody 61C6 had a dynamic range of 10-30,000 ng/mL, and LDL<5.0 ng/mL. The functional sensitivity was determined to be approximately 10 ng/mL (which is an estimate of functional sensitivity based on the calibrator curve). The 5-FU assay with antibody 61C6 had less than 3.0% cross-reactivity to uracil, DH-5-FU, capecitabline, uridine, thymine, thymidine, folinic acid, oxaliplatin, irinotecan, methotrexate, cisplatin, and 5-ethynyluracil, and less than 12% cross-reactivity to tegafur.

Example 15

Synthesis and Preparation of Reagents for Various 5-FU Assays Preparation of 1-5C-5-FU-BSA 5-FU was first conjugated to BSA by mixing 1-5C-5-FU-NHS ester with BSA at a challenge ratio of 12:1 (molar ratios of 1-5C-5-FU-NHS to BSA) in a phosphate buffer containing a phosphate buffered saline containing 10.5 mM $KH_2PO_4$, 139.5 mM $K_2HPO4$ and 150.6 mM NaCl, =pH 7.7-7.9 (typically pH 7.8) for a 1 hour or more incubation at room temperature (typically 1 hour incubation at room temperature). After the incubation, unbound 1-5C-5-FU-NHS ester was removed by 3 buffer exchanges in an AmiconUltra4-30K filter (Millipore, Cat#UFC803024). BSA conjugated with 5-FU (5-FU-BSA) was concentrated and stored in the same phosphate buffer (pH 7.8).

To the prepare Biotin 1-5C-5-FU-BSA (Bi-5C-5-FU-BSA), the 5-FU-BSA was incubated with EZ-Link Sulfo-NHS-LC-Biotin, No-Weigh Format (Thermo Scientific, Cat#21327) at a challenge ratio of 10:1 (molar ratios of EZ-Link Sulfo-NHS-LC-Biotin to 1-5C-5-FU-BSA) in the pH 7.8 phosphate buffer for more than 1 hour at room temperature. After the incubation, unbound EZ-Link Sulfo-NHS-LC-Biotin was removed by 3 buffer exchanges in an AmiconUltra4-30K filter (Millipore, Cat#UFC803024) into a pH 7.2 phosphate buffered saline (PBS) containing 37.5 mM $KH_2PO_4$, 112.5 mM $K_2HPO_4$, 150.6 mM NaCl and 0.10% 2-Methyl-4-isothiazolin-3-one Hydrochloride (MIT).

To prepare TAG Plus 1-5C-5-FU-BSA, the 5-FU-BSA was incubated with TAG Plus NHS ester at a challenge ratio of 12:1 (molar ratios of TAG Plus NHS ester to 1-5C-5-FU-BSA) in the pH 7.8 phosphate buffer for typically 1 hour at room temperature. After the incubation, unbound TAG Plus NHS ester was removed by 3 buffer exchange in an AmiconUltra4-30K filter (Millipore, Cat#UFC803024) into a pH 7.2 phosphate buffered saline (PBS) containing 37.5 mM $KH_2PO_4$, 112.5 mM $K_2HPO_4$, 150.6 mM NaCl and 0.10% 2-Methyl-4-isothiazolin-3-one Hydrochloride (MIT).

The preparations of TAG Plus 1-3C-5-FU-BSA and Biotin 1-3C-5-FU-BSA (Bi-1-3C-5-FU-BSA) were similar to the preparation of TAG Plus 1-5C-5-FU-BSA and Biotin 1-5C-5-FU-BSA. The 5-FU with a 3 carbon linker was first conjugated to BSA by incubating 1-3C-5-FU-NHS ester with BSA. The 1-3C-5-FU-BSA was then conjugated with TAG Plus NHS ester and with EZ-Link Sulfo-NHS-LC-Biotin at challenge ratios of 12:1 and 10:1, respectively.

The preparations of TAG Plus 3-5C-5-FU-HSA and Biotin 3-5C-5-FU-HAS (Bi-3-5C-5-FU-HAS) were essentially the same as described for the preparation of TAG Plus 1-5C-5-FU-BSA and Biotin 1-5C-5-FU-BSA. Except a human serum albumin (HSA) was first conjugated with a 5-FU 3-position modified NHS ester (3-5C-5-FU NHS ester) and the 3-5C-5-FU-BSA was further modified with EZ-Link Sulfo-NHS-LC-Biotin and TAG Plus NHS ester.

With reference now to FIG. 1, to prepare 1-5C-5-FU-M270 Beads and 1-3C-5-FU-M270 Beads the following scheme was followed. See [6c] of FIG. 1. Dynabeads M-270 Amine (15 mg, 500 uL, Invitrogen, Cat#14307D) was pipetted to a 1.5 mL microtube, washed with 3×1000 μL of 0.2N carbonate-bicarbonate (Thermo Scientific, Cat#28382) buffer (pH9.4) and suspended in 0.75 mL of carbonate-bicarbonate buffer. A solution of [4] (12 mg in 0.25 mL of anhydrous N,N'-dimethylformamide) in FIG. 1 was added to the pre-treated beads and the resulting mixture was shaken at room temperature for 4 h. The supernatant was removed under magnet, washed with 1×1000 μL of N,N'-dimethylformamide and 2×1000 μL of PBST buffer. The resulting beads were reconstituted in 500μL of PBST buffer. See [6d] of FIG. 1. The same procedure as described in [6c] was used for preparation of [6d] in FIG. 1.

The scheme for preparation of TAG Plus 1-3C-5-FU was as follows:

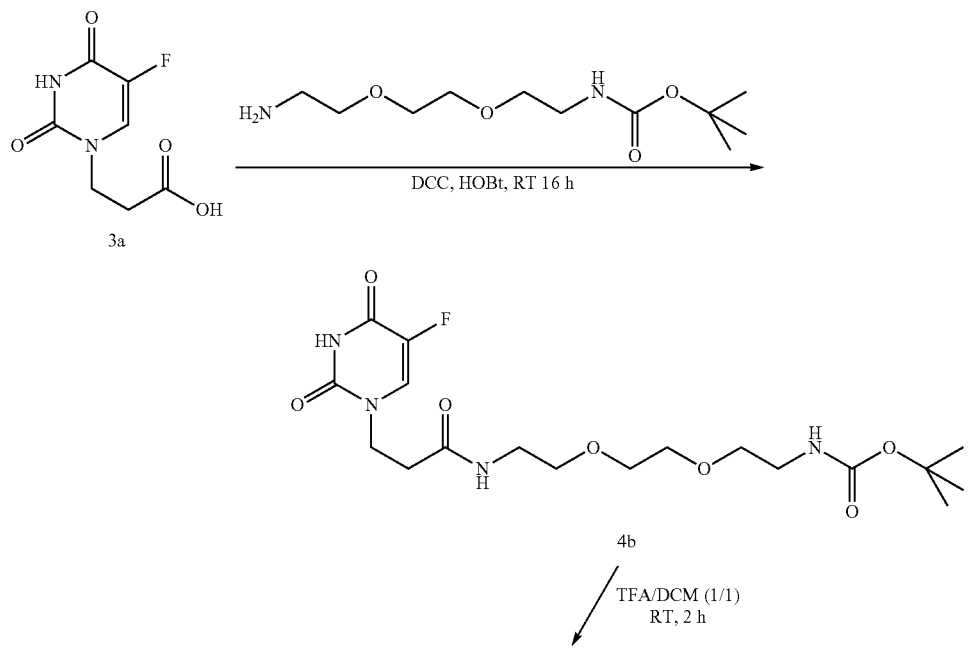

-continued

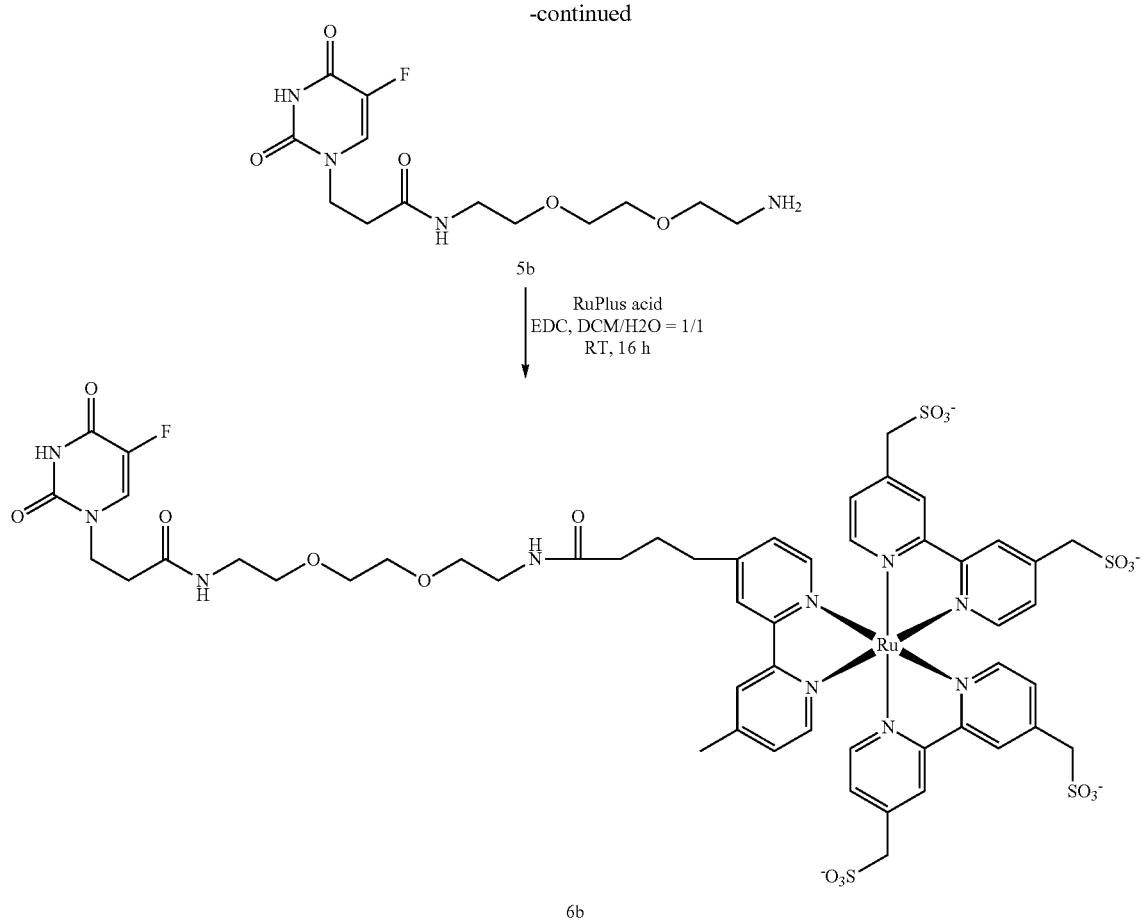

[4b] To a mixture of [3a] (350 mg) in 60 mL of dichloromethane (Sigma-Aldrich, Cat#270997-1 L) was added N-Boc-2,2'-(ethylenedioxy)diethylamine (376 mg, Sigma-Aldrich, Cat#89761-1G) under argon. Dicyclohexylcarbodiimide (315 mg, Sigma-Aldrich, Cat#D80002-25G) and 1-Hydroxybenzotriazole (186 mg, Sigma-Aldrich, Cat#362441-50G) were added to the above mixture. The resulting mixture was stirred at room temperature under argon overnight. Upon completion, the mixture was concentrated and purified over a flash column employing 0-3% methanol in dichloromethane as eluent to yield 600 mg of product.

[5b] To [4b] (56 mg) in dichloromethane (2 mL, Sigma-Aldrich, Cat#270997-1L) was added 2 mL of triethylamine (Sigma-Aldrich, Cat#T0886-1L). The resulting mixture was stirred at room temperature for 3 hours. The solvent was removed under reduced pressure. 2×30 mL of dichloromethane (containing 1% triethylamine) was added and the solvent was removed under reduced pressure to yield 50 mg of product.

[6b] To a mixture of 50 mg of [5b] in 4 mL of dichloromethane/water (1/1) was added 55 mg of RuPlus acid (BioVeris). 1-ethyl-3-(3-dimethylamino)propyl carbodiimide (25 mg, Sigma-Aldrich, Cat.#E7750-25G). and 1-Hydroxybenzotriazole (HOBt, 15 mg, Sigma-Aldrich, Cat#362441-50G) were added and the resulting mixture was stirred at room temperature under argon for 16 h. The solvent was removed under reduced pressure. The reaction mixture was redissolved in water and applied to a DEAE Sephadex A-25 (Sigma-Aldrich, Cat#A25120-100G) ion exchange column (2.5 cm×10 cm) that has been equilibrated with: 1) 1.0M triethylammonium buffer (TEAB, Sigma-Aldrich, Cat#T7408) (pH7.6, 50 mL), 2) 1.0M sodium bicarbonate (25 mL) and 3) 0.1M TEAB (pH7.6, 50 mL). The column was eluted with a gradient of 0.1M (pH7.6) to 0.4M TEAB (pH7.6) to yield the desired product.

To purify the monoclonal 61C6, the culture supernatant of monoclonal antibody 61C6 (about 100 mL) was harvested and stored in 50-mL conical tubes. The supernatant was clarified by centrifugation at 3,500 g for 10 minutes in a desk top centrifuge and filtered through a 0.2 µm filter unit and diluted with 100 mL of IgG Protein A Binding Buffer. The diluted supernatant was mixed with 2.0 mL of Protein A resin slurry (Thermo Science), which was washed once in a 15 mL conical tube with 5.0 mL of Protein A Binding Buffer (Thermo Science) overnight at 2-8C. After the incubation, the Protein A resin was then transferred to a 15 mL conical tube and was washed 4 times with 5 mL Protein A IgG Binding Buffer and transferred to a 2 mL spin column. Antibody was eluted from the column in IgG Elution buffer and the elutants were neutralized immediately with 1.0 M Tris-HCl pH 8 (0.15 mL for 1.0 mL elution). The eluted antibody was buffer exchanged into a phosphate buffer pH 7.8.

To the prepare Bi mAb 61C6, the purified mAb 61C6 was incubated with EZ-Link Sulfo-NHS-LC-Biotin, No-Weigh Format (Thermo Scientific, Cat#21327) at a challenge ratio of 8:1 (molar ratios of EZ-Link Sulfo-NHS-LC-Biotin to mAb 61C6) in the pH 7.8 phosphate buffer for typically 1 hour at room temperature. After the incubation, unbound EZ-Link Sulfo-NHS-LC-Biotin was removed by 3 buffer exchange in an AmiconUltra4-30K filter (Millipore, Cat#UFC803024) into a pH 7.2 phosphate buffered saline (PBS) containing 37.5 mM $KH_2PO_4$, 112.5 mM $K_2HPO_4$, 150.6 mM NaCl and 0.10% 2-Methyl-4-isothiazolin-3-one Hydrochloride (MIT).

To prepare TAG Plus mAb 61C6, the purified mAb 61C6 was incubated with TAG Plus NHS ester at a challenge ratio of 15:1 (molar ratios of TAG Plus NHS ester to mAb 61C6) in the pH 7.8 phosphate buffer for typically 1 hour at room temperature. After the incubation, unbound TAG Plus NHS ester was removed by 3 buffer exchange in an AmiconUltra4-30K filter (Cat: UFC803024. Millipore, Billerica, Mass.) into a pH 7.2 phosphate buffered saline (PBS) containing 37.5 mM $KH_2PO_4$, 112.5 mM $K_2HPO_4$, 150.6 mM NaCl and 0.10% 2-Methyl-4-isothiazolin-3-one Hydrochloride (MIT).

To prepare Biotin-anti-5-FU 61C6 monoclonal antibody pre-bound to M280-Streptavidin beads (M280-SA), 1.0 mg M280-SA beads (Invitrogen, Cat#112-05D) were incubated with 8.0 µg Bi anti-5-FU 61C6 monoclonal antibody in Sample Buffer (described below) for one hour at room temperature. After one hour incubation, the Biotin-anti-5-FU 61C6 monoclonal antibody-M280-SA beads complexes were washed 3 times with the Sample Buffer and were re-suspended in Sample Buffer at 1.0 mg/mL. The pre-bound Bi anti-5-FU 61C6 monoclonal antibody-M280-Streptavidin beads were stored at 2-8° C.

Example 16

Optimization of 5-FU Reagent Concentration in 5-FU ECL Assay

This experiment was performed to optimize concentration of 5-FU reagents utilizing assay format of biotinylated anti-5-FU 61C6 monoclonal antibody-Streptavidin beads (Bi-mAb-Beads) as capture, and TAG Plus 1-5C-5-FU-BSA as detector.

The optimization was performed using an eight point calibrator curve and checkerboard titrations with detector reagent (TAG Plus 1-5C-5-FU-BSA) concentration at 0.2 µg/mL and capture reagent (Bi-mAb-Beads) concentrations at 0.1, 0.15, 0.2, and 0.25 mg/mL.

The assay was prepared using the following protocol. The 5-FU capture reagent was Bi-mAb-Beads and was tested at various concentrations of 0.1, 0.15, 0.2, and 0.25 mg/mL in Sample Buffer. The detector reagent was TAG Plus 1-5C-5-FU-BSA and was tested at a concentration of 0.2 µg/mL in Sample Buffer. 5-FU reagents (capture and detector) were used as an aqueous form in this experiment.

The Sample Buffer was formulated with the following component concentrations: 100 mM Sodium Phosphate with 0.03% Tween-20; 150 mM Sodium Chloride (NaCl) with 0.05% Proclin 300; 0.5% Bovine Serum Albumin (BSA) with 0.025 mg/mL HRB1; 0.5% Bovine IgG (BGG) with 0.05 mg/mL MAK-33 IgG Poly; 15% Trehalose with 2% PEG; and 2.5 mg/mL Salicylic Acid with 10 µg/mL Goat anti-mouse IgG.

The following materials were used in the assay preparation: Milli-Q water (MilliQ); Sodium Dihydrogen Phosphate ($NaH_2PO_4$) (Sigma); Sodium Phosphate Dibasic ($Na_2HPO_4$) (Sigma); Sodium Chloride (NaCl) (Sigma); Trehalose (Fisher); PEG (Sigma); Goat Anti-Mouse IgG (Thermo Scientific); MAK33-$I_g$G Poly (Roche); HBR-1 (Scantibodies); Proclin 300 (Sigma); 0.2 µm Disposable Filter Unit (VWR); Bovine Serum Albumin (BSA) (Sera Care); Bovine $I_g$G (BGG) (Millipore); Tween-20 (BioChem); Salicylic Acid (Sigma); 1.0N NaOH (JT Baker); pH 4 Buffer (VWR); pH 7 Buffer (VWR).

A clean 1000 mL disposable beaker was filled with approximately 300 mL (300 g) of DI Water. A stir bar was added to the beaker and the beaker placed on a stir plate mixing at a moderate speed.

The following materials were added to the beaker and mixed until all solids were visibly dissolved: $NaH_2PO_4$, $Na_2HPO_4$, NaCl, Trehalose, PEG. Next, the following materials were added to the beaker with continued mixing until visibly dissolved: BSA, BGG, Tween-20, Proclin300, Salicylic Acid, Mouse IgG, MAK33-$I_g$G poly, HBR-1. 1.0N NaOH was used to adjust the pH of the solution to 7.1±0.1 using a pH meter calibrated to the 4-7 range. The solution was brought to a final volume of 500 mL using a graduated cylinder and mixed for a minimum of 10 minutes. Using an aspirator pump, the solution was filtered through a 0.2 µm sterile filter unit.

A calibrator curve was formulated with 5-FU antigen (Sigma Aldrich, Cat#858471) in charcoal stripped lithium heparin human plasma (BioReclamation, Cat#HMPLLIHP-STRPD) at concentrations of 0.0, 50, 100, 250, 625, 2500, 10000, and 20000 ng/mL was prepared. GLO Solution was prepared with 4.1% potassium phosphate, monobasic; 2.14% tripropylamine (TPA); 0.88% sodium chloride; 0.02% Polidocanol [Thesit]; and 0.1% Oxaban-A preservative). STORE Solution was prepared with 0.02% Polidocanol [Thesit], and 0.12% Kathon CG-ICP.

The following equipment was used in the assay procedures: LifeSep 96F Plate Magnet (Dexter Magnetic Technologies); Vortex Genie (VWR); Picofuge Centrifuge (VWR); Timer (VWR); 96 well Round Bottom Plate (Greiner (Cat#650201)); Digital Heat Block (VWR); Micromix Plate Shaker (Seimens/DPC).

The following assay was run on an electrochemiluminescent (ECL) based detection analyzer, BioVeris M1M (Cat#310806), modified for sample volume. The modifications are as follows. Tubing lengths were shortened where applicable, and the flow cell inlet hole diameters and measurement area and volume are reduced. The software used on the analyzer is a research version of the software that allows for adjustable parameters. The sequence of operation parameters were also modified for sample volume in this research software. An instrument with these modifications was designated MeM1.

The following assay is a competitive format assay, e.g., as the concentration of the detected analyte increases the signal from the assay decreases. The assay procedure was as follows. On a metal plate holder of a Digital Heat Block set at 37±2° C., 50 µL of each calibrator followed with 26 µL of capture and 26 µL of detector reagent in duplicate were added directly into plate wells. The plates were placed on the Micromix shaker set at Form 8 & Amp 6 for 30 seconds to mix. The plates were then placed in the metal plate holder of a Digital Heat Block set at 37±2° C. The plate was covered with a plate cover and incubated for 5±0.5 minutes. Following the assay incubation, assay plate was washed 2× with 150 µL/well of GLO solution. The magnetic bead complex in each plate well was pelleted on a plate magnet for 2±0.5 minutes. The liquid content from each well was decanted into an appropriate waste container, and residual liquid was removed by quickly striking the plate against a stack of paper towels. 150 µL of GLO Solution was added to each well. The plate was re-suspended and washed on the Micromix shaker set at Form 8 & Amp 6 for 2±0.5 minutes. Each of the above steps was repeated one additional time. After the second wash, the washed bead complex was re-suspended in 100 μL/well of GLO Solution. The plate was placed on the Micromix shaker set at Form 8 & Amplitude 6 for 2±0.5 minutes to completely re-suspend the beads. The plates were evaluated on an MeM1 analyzer using the single buffer system (GLO Solution). The plate was evaluated using Wasabi version 2.02.0039.

Results for the 0.2 μg/mL TAG Plus 1-5C-5-FU-BSA study showed that the antibody configuration of 0.25 mg/mL capture reagent and 0.2 μg/mL detector reagent generated better data when compared to the other tested conditions (e.g., 0.15 mg/mL Capture, 0.1 mg/mL Capture) with highest mean ECL counts, and % CV for ECL and quantitation below 6%. This antibody configuration was found to be acceptable for a 5-FU immunoassay. The nonzero calibrators (CAL2-CAL8) for the 5-FU immunoassay spanned the range of 50 ng/mL to 20,000 ng/mL (specifically, 50, 100, 250, 625, 2500, 10000, 20000 ng/mL).

Example 17

Cross-Reactivity Evaluation

This experiment was performed to test the specificity of the monoclonal antibody 61C6 against 5-FU analogues, pro-drugs and interference reagents. The components of 5-FU assay (capture, detector) have been evaluated in aqueous forms and were also used in Example 16. In this Example, the components of 5-FU assay (capture, detector) were lyophilized and the sample (calibrator, controls, and spiked plasma samples) were added directly to the lyophilized reagent pellets.

The chemicals, pro-drugs and interference reagents and their tested concentrations were as follows: 10 μg/mL of each of Uracil, Uridine, Thymine, Thymidine, DH5FU, Tegafur, Capecitabine, and Hemoglobin; 100 μg/mL of each of Folinic Acid, Oxaliplatin, Irinotecan, Methotrexate, and Cisplatin; 0.6 mg/mL of Bilirubin; and 30 mg/mL of Intralipid.

The assay was prepared using the following protocol. The 5FU capture reagent had Bi-mAb-Beads at a concentration of 0.325 mg/mL in sample buffer (Example 16). The detector reagent had TAG Plus 1-5C-5-FU-BSA at a concentration of 0.26 μg/mL in sample buffer (Example 16). The capture and the detector solutions were aliquoted (20 μL) and lyophilized. A calibrator curve formulated with 5-FU antigen in charcoal stripped lithium heparin human plasma at concentrations of 0.0, 25, 100, 250, 625, 2500, 10000, and 20000 ng/mL was prepared. Three levels (high, mid, and low) of control samples (15000, 1500, and 75 ng/mL) formulated with 5-FU antigen in charcoal stripped lithium heparin human plasma were prepared. 15 compounds that possibly might have cross reactivity with the assay antibody were tested to ascertain the extent and nature of the reactivity. Compounds were spiked (at a concentration of 10,000 ng/mL for endogenous, 100,000 ng/mL for exogenous) into 5-FU free samples, 75 ng/mL spiked 5-FU samples, and 1,000 ng/mL spiked 5-FU samples.

The following compounds were used in the assay: Uracil (Sigma Aldrich, #019K0033); Uridine (Sigma Aldrich, #030M5309V); Thymine (Sigma Aldrich, #0001438242); DH5FU (Medical Isotopes, #10310); Tegafur (Acros Organics, #A001543501); Capecitabine (Toronto Research Chemicals, Inc., #TRC-040306); Folinic Acid (Sigma Aldrich, #BCBC4176V); Oxaliplatin (Sigma Aldrich, #09512); Irinotecan (Sigma Aldrich, #050M1580V); Methotrexate (MP Biomedicals, LLC, #R27204); Cisplatin (Sigma Aldrich, #479306); Bilirubin (Sigma Aldrich, #106K1562); Hemoglobin (Sigma Aldrich, #069K7545); Intralipid (Sigma Aldrich, #028K0740).

The following equipment was used in the assay procedures: LifeSep 96F Plate Magnet (Dexter Magnetic Technologies); Vortex Genie (VWR); Picofuge Centrifuge (VWR); Timer (VWR); 96 well Round Bottom Plate (Greiner (Cat#650201)); Digital Heat Block (VWR); Micromix Plate Shaker (Seimens/DPC).

The assay procedure was as follows. The electrostatic on the surface of the microplate was reduced by using a Zerostat Antistatic Device prior to use. The device was pointed on the surface of the microplate, squeezed and the trigger released a few times across the microplate. 1 lyophilized pellet of each capture and detector reagent was transferred into plate wells using the Vacuum Pick-Up System. A hollow needle tip was attached onto the pick-up pen, and the finger controlled vacuum was used for picking up (the index finger was placed over the hole so that vacuum was drawn through the needle) or releasing pellet (lifting the index finger off of the hole). On a metal plate holder of a Digital Heat Block set at 37±2° C., 50 μL of each calibrator, control, and sample (in this case cross-reactivity panels) were added in duplicate directly into plate wells containing 2 lyophilized pellets. The plate was placed on the Micromix shaker set at Form 8 & Amp 6 for 30 seconds to mix. The plate was then placed in the metal plate holder of a Digital Heat Block set at 37±2° C. The plate was covered with a plate cover and incubated for 5±0.5 minutes. Following the assay incubation, the assay plate was washed and evaluated as described in Example 16.

TABLE 6

Data Summary

| Chemicals | Concentration Tested | Without 5-FU | | With 75 ng/mL Spiked 5-FU | | With 1000 ng/mL Spiked 5-FU | |
|---|---|---|---|---|---|---|---|
| | | Measured Value (ng/mL) | % Cross-React | Measured Value (ng/mL) | % Cross-React | Measured Value (ng/mL) | % Cross-React |
| Uracil | 10 μg/mL | 186 | 1.9 | 419 | 3.4 | 1258 | 2.6 |
| Uridine | 10 μg/mL | 48 | 0.5 | 234 | 1.6 | 1094 | 0.9 |
| Thymine | 10 μg/mL | 99 | 1.0 | 322 | 2.5 | 1224 | 2.2 |
| Thymidine | 10 μg/mL | 17 | 0.2 | 178 | 1.0 | 1131 | 1.3 |
| DH5FU | 10 μg/mL | NT | NT | NT | NT | 1095 | 1.0 |
| Tegafur | 10 μg/mL | 4229 | 42 | 5723 | 56 | 5543 | 45 |
| Capecitabine | 10 μg/mL | 1.9 | 0.0 | 143 | 0.7 | 1058 | 0.6 |

TABLE 6-continued

Data Summary

| Chemicals | Concentration Tested | Without 5-FU | | With 75 ng/mL Spiked 5-FU | | With 1000 ng/mL Spiked 5-FU | |
|---|---|---|---|---|---|---|---|
| | | Measured Value (ng/mL) | % Cross-React | Measured Value (ng/mL) | % Cross-React | Measured Value (ng/mL) | % Cross-React |
| Folinic Acid | 100 μg/mL | 0.8 | 0.0 | 129 | 0.1 | 965 | 0.0 |
| Oxaliplatin | 100 μg/mL | NT | NT | NT | NT | 971 | 0.0 |
| Irinotecan | 100 μg/mL | 4.8 | 0.0 | 139 | 0.1 | 1266 | 0.3 |
| Methotrexate | 100 μg/mL | 1.1 | 0.0 | 108 | 0.0 | 1106 | 0.1 |
| Cisplatin | 100 μg/mL | NT | NT | NT | NT | 1116 | 0.1 |
| Bilirubin | 60 mg/dL or 0.6 mg/mL | 96 | 0.0 | 220 | 0.0 | 968 | 0.0 |
| Hemoglobin | 10 mg/mL | 234 | 0.0 | 322 | 0.0 | 950 | −0.1 |
| Intralipid | 3000 mg/dL or 30 mg/mL | 17 | 0.0 | 129 | 0.0 | 825 | 0.0 |

NT = not tested; Cross-reactivity did not exceed 2% with the exception of two compounds: Uracil: 2.6% and Tegafur: 47.7%.

Results demonstrated that lyophilized 5-FU reagents work well and that neat plasma (100% matrix) can be tested with lyophilized 5-FU reagents.

Example 18

Evaluation of 5-FU Lyophilized Reagent Precision

This experiment evaluated the 5-FU lyophilized reagent precisions over 5 runs on two different MeM1 analyzers. The materials and equipment used were the same as those described in Example 17. The protocol used was the same as that described in Example 17.

Overall, calibrator and control samples met the expected acceptance criteria: CV %<10%; % AR=±20% of target value with the exception of one high control, which was over-quantitated (151%) but met the specification of 2 of 3 controls within 20% of nominal. Results from the five runs for 5-FU calibrators and quality controls included: Average % CV for ECL (calibrators & controls)=3.5%; and Average % CV for quantitation (calibrators & controls)=4.6%. Consistent results from the 5 runs indicated that the 5-FU immunoassay has satisfactory precision indicated by the low % CV.

Example 19

Assay Low Detection Limit (LDL) Evaluation

This experiment was performed to evaluate 5-FU assay sensitivity by assessing low detection limit (LDL) from 80 points of CAL1 (zero calibrator) over 2 runs. The evaluation was based on 8-point calibrator curve and trilevel controls. The materials and equipment used were the same as those described in Example 16. The protocol used was the same as that described in Example 17.

The average LDL value from the two runs was determined to be 2.54 ng/mL with average % CV for ECL=3.39%.

Example 20

Assay Timing Evaluation

This experiment was performed to evaluate the 5-FU immunoassay incubation timing. The assay incubation time of 5, 10, and 15 minutes at 37° C. was tested and was based on an 8-point calibrator curve and trilevel controls. The materials and equipment used were the same as those described in Example 17. The protocol used was the same as that described in Example 17 except that each assay plate was incubated for 5±0.5 minutes, 10±1 minutes, and 15±1.5 minutes consecutively. One MeM1 and one lot of prepared and frozen calibrators and controls were used for the study.

The ECL signal progressively increased as the assay incubation time extended from 5 to 15 minutes at 37° C. At 15 minutes incubation, the ECL counts were about one million counts, which is not recommended since the signal has reached the saturation ranges of the instrument.

The assay sensitivity was noticeably diminished as the assay incubation time extended from 5 to 15 minutes at 37° C. (the % difference in signal of each calibrator compared to CAL1 (0.0 ng/mL 5-FU, zero calibrator)). At 5 minutes incubation, the ECL signal dropped to 61% when 25 ng/mL of 5-FU was spiked into charcoal stripped plasma (CAL2, 25 ng/mL 5-FU) compared to CAL1 while with the same level of spiked 5-FU, the ECL signal only dropped to 78% in comparison to CAL1 at other incubation timing, indicating that the 5-FU immunoassay achieves better sensitivity at shorter incubation time. Results demonstrated that 5 minutes at 37° C. was the optimal assay timing for 5-FU immunoassay.

Example 21

Evaluation of 5-FU Sample Buffer

These experiments were performed to evaluate if the addition of salicylic acid and/or goat anti-mouse is needed in the 5-FU Sample Buffer, for example, to help reduce detection of elevated 5-FU counts in some normal plasma samples. These experiments used four different formulations of the 5-FU Sample Buffer and were evaluated by two different operators.

The four different formulations of 5-FU Sample Buffer were as follows referring to the Sample Buffer of Example 16 for the components and their concentrations: Formulation I—no salicylic acid (otherwise same as Sample Buffer in Example 16); Formulation II—no goat anti-mouse IgG (otherwise same as Sample Buffer in Example 16); Formulation III—no salicylic acid and no goat anti-mouse IgG (otherwise same as Sample Buffer in Example 16); and Formulation IV—same as Sample Buffer in Example 16, i.e., contains both salicylic acid and goat anti-mouse IgG. The materials and equipment used were the same as those described in Example 16. The protocol used was the same as that described in Example 16.

Results for the Evaluation of 5-FU Sample Buffers were collected and analyzed, looking at mean ECL counts and mean concentration for the calibrators and spiked human plasma samples with the assays performed by two operators. All of the results represent the average of two wells for the calibrator and controls and three wells for the normal and spiked plasma samples.

The spiked sample quantitation was based on an 8-point calibrator curve and trilevel control samples. A total of thirty-two assay plates were evaluated by two operators (16 assay plates per operator) on two different MeM1 analyzers. Each assay plate consisted of an 8-point calibrator curve, tri-level control, and spiked normal human plasma samples. The normal human plasma samples (total of 15) were each spiked at 3 levels of 5-FU analyte (0, 500, and 5000 ng/mL). During testing the 15 samples were run in groups of 3 or 4 with each buffer formulation. Each buffer formulation required 4 plates to evaluate the 15 spiked normal human plasma samples.

Calibrator curves from all plates (32 plates between two operators) met the following exemplary acceptance criteria for the 5-FU immunoassay: Six out of seven calibrators, from Cal 2-Cal 8 (25, 100, 250, 500, 1000, 2500, 10000 ng/mL, respectively) have acceptable % coefficient variations (% CVs) for counts and quantitation. For Cal 2 and Cal 8, % CVs for counts and quantitation 20% are acceptable. For Cal 3-Cal 7 (100, 250, 500, 1000, 2500 ng/mL, respectively), % CVs for counts and quantitation ≤15% are acceptable. Cal 3-Cal 7 backfit within ±15% of target concentration. Cal 2 and Cal 8 backfit within ±20% of target concentration. These limits ensure that the quality of the calibrator curve fit is such that accurate quantitation of samples and controls is feasible. A maximum of 1 calibrator between Cal 2-Cal 8 may be removed if the back-fit or % CVs are outside of the acceptable criteria, leaving a minimum of 6 calibrators to generate the four parameter logistic curve fit.

Two out of three controls quantitated within ±20% of the target value. The Calibrator % CV for counts and quantitation from all plates were ≤5%. Calibrator back-fit also met the exemplary acceptance criterion of back-fit±20% for calibrator 3-7, and ±15% for Cal 2 and Cal 8. The Control % CV for counts and quantitation from all plates were ≤20%. Control back-fit also met the acceptance criterion of backfit within 20% of target.

The ECL signals for calibrator and control samples using different formulations of 5-FU Sample Buffers were comparable in terms of % CV for ECL and quantitation. The ECL signals obtained from the operator #2 experiments were 10-15% lower when compared to those from the operator #1 experiments. Although, not wishing to be bound by theory, the reduction in ECL signals was likely due to (1) the Capture Reagents in liquid form being three weeks old when operator #2 finished the testing and/or (2) the differences between analyzers. The reduced ECL signals did not affect the quantitation of spiked plasma samples.

The 5-FU values quantitated from the spiked human plasma samples using different formulations of 5-FU Sample Buffers also had similar results to each other.

The overall results from this study demonstrated that the addition of salicylic acid and goat anti-mouse IgG in the 5-FU Sample Buffer do not cause a significant reduction in the background quantitation of 5-FU in normal human plasma samples.

Most of the 5-FU immunoassays disclosed herein were run on MeM1 Analyzer instrument using ECL technology as the detection method. The incubation time was about 5 minutes at 37° C. The samples contained human plasma, lithium heparin anticoagulated with sample volumes at 50 μL, with the following controls: 75 ng/mL, 1500 ng/mL, 15000 ng/mL 5-FU. A calibrator range of 0.0-20,000 ng/mL 5-FU was used with 5 Parameter Logistic, Weighting of 1/(Signal) calibrator curve.

Example 22

Amino Acid and Nucleotide Sequences of mAb 61C6 Heavy Chain of mab 61C6

The nucleotide sequence coding for the heavy chain of mab 61C6 was determined to be SEQ ID NO:10.

The amino acid sequence of the heavy chain of mab 61C6 was determined to be:

```
                                              (SEQ ID NO: 2)
MDWLWNLLFLMAAAQSIQAQIQLVQSGPELKKPGETVTISCKAS

GYTLTNYGMNWVKQAPGKGLKWMGWINTNSGEPTYVEEFKGRFA
CDR-H1                  CDR-H2

FSLETSVSTVYLQISDLKHEDTATYFCARWGPHFNAYGWFAYWG
                                CDR-H3  CDR-H3

QGTLVTVSAAKTTPPSVYPLAPGCGDTTGSSVTLGCLVKGYFPE

SVTVTWNSGSLSSSVHTFPALLQSGLYTMSSSVTVPSSTWPSQT

VTCSVAHPASSTTVDKKLEPSGPISTINPCPPCKECHKCPAPNL

EGGPSVFIFPPNIKDVLMISLTPKVTCVVVDVSEDDPDVQISWF

VNNVEVHTAQTQTHREDYNSTIRVVSTLPIQHQDWMSGKEFKCK

VNNKDLPSPIERTISKIKGLVRAPQVYILPPPAEQLSRKDVSLT

CLVVGFNPGDISVEWTSNGHTEENYKDTAPVLDSDGSYFIYSKL

NMKTSKWEKTDSFSCNVRHEGLKNYYLKKTISRSPGK
```

The amino acid sequence of the heavy chain of mab 61C6 (SEQ ID NO:2) contains a putative signal peptide (1-19), CH1 (142-238) and CH2 (261-370) regions (underlined). The hinge region (239-370) is in italics. The CDR-H1 (45-54) (SEQ ID NO:3), CDR-H2 (69-85) (SEQ ID NO:4) and CDR-H3 (118-130) (SEQ ID NO:5) regions are also underlined.

The nucleotide sequence coding for the light chain of mab 61C6 was determined to be as in SEQ ID NO:11.

The amino acid sequence of the light chain of mab 61C6 was determined to be:

```
                                              (SEQ ID NO: 6)
MMSSAQFLGLLLLCFQGTRCYIQMTQTASSLSASLGDRVTISCRASQDI

WNYLNWYQQKPDGTIKLLIYYKSRLHSGVPSRFSGSGSGIDFSLTISNL

EQEDFATYFCQQGHTLPWTFGGGSKLEIKRADAAPTVSIFPPSSEQLTS

GGASVVCFLNNFYPKDINVKWKIDGSERQNGVLNSWTDQDSKDSTYSMS

STLTLTKDEYERHNSYTCEATHKTSTSPIVKSFNRNEC
```

The amino acid sequence of the light chain of mab 61C6 (SEQ ID NO:6) contains a putative signal peptide (1-20), CDR-L1 (44-54) (SEQ ID NO:7), CDR-L2 (70-76) (SEQ ID NO:8) and CDR-L3 (109-117) (SEQ ID NO:9), all of which are underlined.

What is claimed is:

1. An antibody or fragment thereof that binds to 5-fluorouracil (5-FU), wherein the antibody or fragment thereof comprises the heavy chain amino acid sequence of amino acids 20-477 of SEQ ID NO:2, and the light chain amino acid sequence of amino acids 21-234 of SEQ ID NO:6.

2. A method of detecting 5-fluorouracil (5-FU) in a sample, comprising:
(1) combining in a solution at least said sample with
 (a) a first binding molecule, wherein the first binding molecule comprises an antibody or fragment thereof, wherein the antibody or fragment thereof comprises the heavy chain amino acid sequence of amino acids 20-477 of SEQ ID NO:2, and the light chain amino acid sequence of amino acids 21-234 of SEQ ID NO:6, and is capable of binding 5-FU; and
 (b) a detector molecule comprising a detection label, wherein the detection label is selected from the group consisting of an electrochemiluminescence label, an enzyme label, a fluorophore, a latex particle, a magnetic particle, a radioactive element, a phosphorescent dye, a dye crystalite, a gold particle, a silver colloidal particle, a selenium colloidal particle, a ruthenium metal chelate, an osmium metal chelate a coenzyme, an electro active group, an oligonucleotide and a stable radical,
 wherein the first binding molecule can bind the detector molecule, and
 wherein 5-FU, if present in the sample, competitively inhibits the binding of the first binding molecule to the detector molecule; and
(2) detecting the presence of 5-FU in the sample by detecting a signal or lack thereof from the detection label of the detector molecule after binding to the first binding molecule, wherein the presence of 5-FU is inversely proportional to the binding of the first binding molecule to the detector molecule.

3. The method of claim 2, wherein the sample is a serum sample from a mammal.

4. The method of claim 2, wherein the sample is diluted prior to combining with the first binding molecule.

5. The method of claim 2, wherein the sample is not diluted prior to combining with the first binding molecule.

6. The method of any one of claims 2, 3, 4 and 5, wherein the sample is blood plasma.

7. The method of claim 2, wherein at least the first binding molecule or the detector molecule is from a lyophilized composition that is rehydrated with the sample.

8. The method of claim 2, wherein the first binding molecule is from a lyophilized composition.

9. The method of claim 2, wherein the detector molecule is from a lyophilized composition.

10. The method of claim 2, wherein the first binding molecule and the detector molecule are lyophilized in separate compositions.

11. The method of claim 10, wherein the separate lyophilized compositions are rehydrated with the sample.

12. The method of claim 2, wherein the method has a lower detection limit of <5.0 ng/mL.

13. The method of claim 2, wherein the method has a dynamic range of 10-30,000 ng/mL.

14. The method of claim 2, wherein the method is completed in less than 15 minutes.

15. The method of claim 2, wherein the sample is from a patient and the method further comprises adjusting a patient's dose of 5-FU based on the amount of 5-FU detected in the sample.

16. The method of claim 2, wherein the solution comprises GPRP-NH$_2$ (SEQ ID NO:1).

17. The method of claim 2, wherein the first binding molecule is bound to a surface.

18. The method of claim 2, wherein after the solution is incubated for a period of time, the first binding molecule is then bound to a surface.

19. The method of claim 18, wherein the first binding molecule and the surface each are comprised of a corresponding member of a binding pair.

20. The method of claim 19, wherein the binding pair is streptavidin and biotin.

21. The method of claim 20, wherein the first binding molecule comprises biotin.

22. The method of any one of claims 17-21, wherein the surface is a bead.

23. The method of claim 22, wherein the bead is a paramagnetic bead.

24. The method of claim 3, wherein the mammal is a human.

25. The method of claim 2, wherein the first binding molecule is produced by immunizing an animal with the compound of the formula with the compound of the formula:

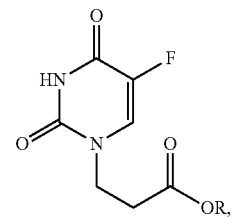

wherein R is the keyhole limpet hemocyanin (KLH).